(12) United States Patent
Yu et al.

(10) Patent No.: US 12,326,491 B2
(45) Date of Patent: Jun. 10, 2025

(54) THERAPEUTIC APPARATUS

(71) Applicant: SHANGHAI UNITED IMAGING HEALTHCARE CO., LTD., Shanghai (CN)

(72) Inventors: Xing'en Yu, Shanghai (CN); Cheng Ni, Shanghai (CN); Peng Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 184 days.

(21) Appl. No.: 17/654,229

(22) Filed: Mar. 9, 2022

(65) Prior Publication Data

US 2022/0193450 A1    Jun. 23, 2022

Related U.S. Application Data

(63) Continuation of application No. PCT/CN2019/104884, filed on Sep. 9, 2019.

(51) Int. Cl.
*G01R 33/38* (2006.01)
*A61B 5/00* (2006.01)
(Continued)

(52) U.S. Cl.
CPC ........ *G01R 33/3804* (2013.01); *A61B 5/0036* (2018.08); *A61N 5/1045* (2013.01);
(Continued)

(58) Field of Classification Search
CPC ............ G01R 33/3804; G01R 33/3815; G01R 33/4812; G01R 33/381; G01R 33/4808;
(Continued)

(56) References Cited

U.S. PATENT DOCUMENTS

2010/0034357 A1    2/2010  Svesson et al.
2010/0160904 A1    6/2010  McMillan et al.
(Continued)

FOREIGN PATENT DOCUMENTS

CN        201177660 Y      1/2009
WO      2014203105 A1    12/2014
(Continued)

OTHER PUBLICATIONS

The Extended European Search Report in European Application No. 19945076.8 mailed on Aug. 22, 2022, 7 pages.
(Continued)

*Primary Examiner* — Jonathan Cwern
(74) *Attorney, Agent, or Firm* — METIS IP LLC

(57) ABSTRACT

A therapeutic apparatus may be provided. The therapeutic apparatus may include a magnetic resonance imaging (MRI) device configured to acquire MRI data with respect to a region of interest (ROI) and a radiation therapy device configured to apply therapeutic radiation to at least one portion of the ROI. The MRI device may include an annular cryostat having one or more chambers, an annular structure assembly and a recess disposed on the annular structure arrangement. The radiation therapy device may at least include an accelerator and one or more collimation components.

20 Claims, 14 Drawing Sheets

(51) Int. Cl.
*A61N 5/10* (2006.01)
*G01R 33/3815* (2006.01)
*G01R 33/48* (2006.01)

(52) U.S. Cl.
CPC ............ *A61N 5/1049* (2013.01); *A61N 5/107* (2013.01); *G01R 33/3815* (2013.01); *G01R 33/4812* (2013.01); *A61N 2005/1055* (2013.01); *A61N 2005/1089* (2013.01); *A61N 2005/109* (2013.01); *A61N 2005/1094* (2013.01)

(58) Field of Classification Search
CPC .. A61B 5/0036; A61N 5/1045; A61N 5/1049; A61N 5/107; A61N 2005/1055; A61N 2005/1089; A61N 2005/109; A61N 2005/1094
See application file for complete search history.

(56) References Cited

U.S. PATENT DOCUMENTS

| | | | | |
|---|---|---|---|---|
| 2011/0043207 | A1* | 2/2011 | Gross | G01R 33/4808 324/318 |
| 2011/0304416 | A1 | 12/2011 | Warner et al. | |
| 2014/0107468 | A1 | 4/2014 | Calvert | |
| 2014/0135615 | A1 | 5/2014 | Kruip | |
| 2014/0275962 | A1 | 9/2014 | Foo et al. | |
| 2015/0255977 | A1* | 9/2015 | Jonas | H02H 7/001 361/19 |
| 2015/0346296 | A1* | 12/2015 | Biber | G01R 33/3804 62/51.1 |
| 2016/0059041 | A1 | 3/2016 | Grodzki et al. | |
| 2016/0136456 | A1* | 5/2016 | Jonas | G01R 33/3815 62/51.1 |
| 2016/0263400 | A1 | 9/2016 | Calvert | |
| 2016/0356869 | A1 | 12/2016 | Dempsey et al. | |
| 2019/0101243 | A1 | 4/2019 | Zou et al. | |
| 2019/0168028 | A1* | 6/2019 | Dempsey | A61N 5/1067 |

FOREIGN PATENT DOCUMENTS

| | | |
|---|---|---|
| WO | 2018053654 A1 | 3/2018 |
| WO | 2021046675 A1 | 3/2021 |

OTHER PUBLICATIONS

International Search Report in PCT/CN2019/104884 mailed on May 27, 2020, 5 pages.

Written Opinion in PCT/CN2019/104884 mailed on May 27, 2020, 6 pages.

* cited by examiner

200

┌─────────────────────────────────────────────┐
│ Acquiring magnetic resonance imaging (MRI) data with │ ～ 202
│ respect to a region of interest (ROI) by an MRI apparatus │
└─────────────────────────────────────────────┘
                        ▼
┌─────────────────────────────────────────────┐
│ Reconstructing an MRI image related to at least one │ ～ 204
│ portion of the ROI based on the MRI data │
└─────────────────────────────────────────────┘
                        ▼
┌─────────────────────────────────────────────┐
│ Determining a parameter associated with a size of the at │ ～ 206
│ least one portion of the ROI based on the MRI image │
└─────────────────────────────────────────────┘
                        ▼
┌─────────────────────────────────────────────┐
│ Generating a control signal according to the parameter │ ～ 208
│ associated with the size of the at least one portion of the │
│ ROI │
└─────────────────────────────────────────────┘
                        ▼
┌─────────────────────────────────────────────┐
│ Sending the control signal to a radiation therapy apparatus │ ～ 210
│ to cause the radiation therapy apparatus to apply an │
│ therapeutic radiation to the at least one portion of the ROI │
└─────────────────────────────────────────────┘

THERAPEUTIC APPARATUS

CROSS-REFERENCE TO RELATED APPLICATIONS

This application is a continuation of International Application No. PCT/CN2019/104884 filed on Sep. 9, 2019, the contents of which are hereby incorporated by reference.

TECHNICAL FIELD

The present disclosure generally relates to a therapeutic apparatus for radiation therapy, and more particularly, relates to the therapeutic apparatus which combines radiation therapy and magnetic resonance imaging technique.

BACKGROUND

Radiation therapy on a lesion (e.g., a tumor) is currently affected by difficulties to track the variation (e.g., motion) of the lesion in different treatment sessions. Nowadays, various imaging techniques may be applied to provide real-time images of the tumor before or within each treatment session. For example, a magnetic resonance imaging (MRI) device may be used in combination with a radiation therapy device to provide MRI images of the lesion. The combination of the MRI device and the radiation therapy device, which forms a therapeutic apparatus, may encounter difficulties in arranging components of the MRI device (e.g., a plurality of main magnetic coils, a plurality of shielding magnetic coils) and components of the radiation therapy device (e.g., a linear accelerator) in a relatively compact space without causing interference. For example, a radiation beam generated by the radiation therapy device may be weakened due to heavy scatter of the radiation beam during the radiation beams pass through a cryostat of the MRI device, which may result in a poor radiotherapy efficacy. Therefore, it is desirable to provide a therapeutic apparatus that provides high therapeutic quality and also has a compact structure as well.

SUMMARY

In a first aspect of the present disclosure, a therapeutic apparatus is provided. The therapeutic apparatus may include a magnetic resonance imaging (MRI) device configured to acquire MRI data with respect to a region of interest (ROI), and a radiation therapy device configured to apply therapeutic radiation to at least one portion of the ROI. The MRI device may include an annular cryostat. The annular cryostat may include one or more chambers arranged along an axis of the annular cryostat, and an annular structure arrangement enclosing the one or more chambers. The annular structure arrangement may include multiple annular structures, and at least one of the multiple annular structures may be made of a metallic material and a reinforcing material. The radiation therapy device may include an accelerator configured to accelerate electrons in an electron beam to produce a photon beam of the therapeutic radiation, and one or more collimation components configured to shape the photon beam. The accelerator may be at least partially located within the recess of the annular cryostat.

In some embodiments, the annular cryostat may further include at least a recess disposed on the annular structure arrangement, the recess having an opening formed on at least one outer surface of the annular structure arrangement.

In some embodiments, the one or more chambers may include two chambers being in fluid communication through a neck portion, and the recess may be at least defined by the two chambers and the neck portion.

In some embodiments, the two chambers may contain a cooling medium, and the neck portion is filled with the cooling medium.

In some embodiments, the annular structure arrangement may include a first annular structure configured to provide a vacuum space enclosing the one or more chambers, a second annular structure configured to reduce heat transfer from the first annular structure to a third annular structure, and a third annular structure configured to contain the cooling medium.

In some embodiments, the cooling medium may include liquid helium.

In some embodiments, the reinforcing material may have one or more characteristics of a low density, a high mechanical strength, a radiation-resistance, or a heat-resistance.

In some embodiments, the reinforcing material may include at least one of a carbon fiber, a glass fiber, an aramid fiber, a silicon carbide (SiC) fiber, an asbestos fiber, a crystal whisker, a graphene fiber, or an alloy material.

In some embodiments, the annular cryostat may further include one or more sensors configured to detect a liquid level of the cooling medium of each of the one or more chambers of the annular cryostat.

In some embodiments, the accelerator may be at least partially surrounded by at least one shielding structure.

In some embodiments, the electron beam may move along an electron beam path that is parallel to the axis of the annular cryostat. The radiation therapy device may further include a target and a beam deflection unit configured to deflect the electrons in the electron beam onto the target to produce the photon beam of the therapeutic radiation.

In a second aspect of the present disclosure, a magnetic resonance imaging (MRI) device is provided. The MRI device may include an annular cryostat. The annular cryostat may include one or more chambers arranged along an axis of the annular cryostat, and an annular structure arrangement enclosing the one or more chambers. The annular structure arrangement may include multiple annular structures, and at least one of the multiple annular structures is made of a metallic material and a reinforcing material.

In some embodiments, a recess may be disposed on the annular structure arrangement, the recess having an opening formed on at least one outer surface of the annular structure arrangement.

In some embodiments, the one or more chambers may include two chambers being connected through a neck portion and in fluid communication through a neck portion, and the recess may be at least defined by the two chambers and the neck portion.

In some embodiments, the two chambers may contain a cooling medium, and the neck portion may be filled with the cooling medium.

In some embodiments, the annular structure arrangement may further include a first annular structure configured to provide vacuum space enclosing the one or more chambers, a second annular structure configured to reduce heat transfer from the first annular structure to a third annular structure, and the third annular structure configured to contain the cooling medium.

In some embodiments, the reinforcing material may have one or more characteristics of a low density, a high mechanical strength, a radiation-resistance, or a heat-resistance.

In some embodiments, the reinforcing material may include at least one of a carbon fiber, a glass fiber, an aramid fiber, a silicon carbide (SiC) fiber, an asbestos fiber, a crystal whisker, a graphene fiber, or an alloy material.

In some embodiments, the annular cryostat may further include one or more sensors configured to detect a liquid level of the cooling medium of each of the one or more chambers of the annular cryostat.

In a third aspect of the present disclosure, a therapeutic apparatus is provided. The therapeutic apparatus may include a magnetic resonance imaging (MRI) device configured to acquire MRI data with respect to a region of interest (ROI), wherein the MRI device includes an annular cryostat, and a radiation therapy device configured to apply therapeutic radiation to at least one portion of the ROI. The MRI device may include an annular cryostat. The annular cryostat may include one or more chambers arranged along an axis of the annular cryostat, and an annular structure assembly enclosing the one or more chambers. The annular structure arrangement may include multiple annular structures and a recess disposed on the annular structure arrangement. At least one of the multiple annular structures may be made of a metallic material and a reinforcing material. The recess may have an opening formed on at least one outer surface of the annular structure arrangement. The radiation therapy device may include an accelerator configured to accelerate electrons in an electron beam along an electron beam path that is parallel to the axis, a target and a beam deflection unit configured to deflect the electrons from the electron beam onto the target to produce a photon beam of the therapeutic radiation. The accelerator may be at least partially located within the recess of the annular cryostat.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 is a flowchart illustrating an exemplary process for applying a therapeutic radiation in a radiation therapy system according to some embodiments of the present disclosure;

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Figure 1:
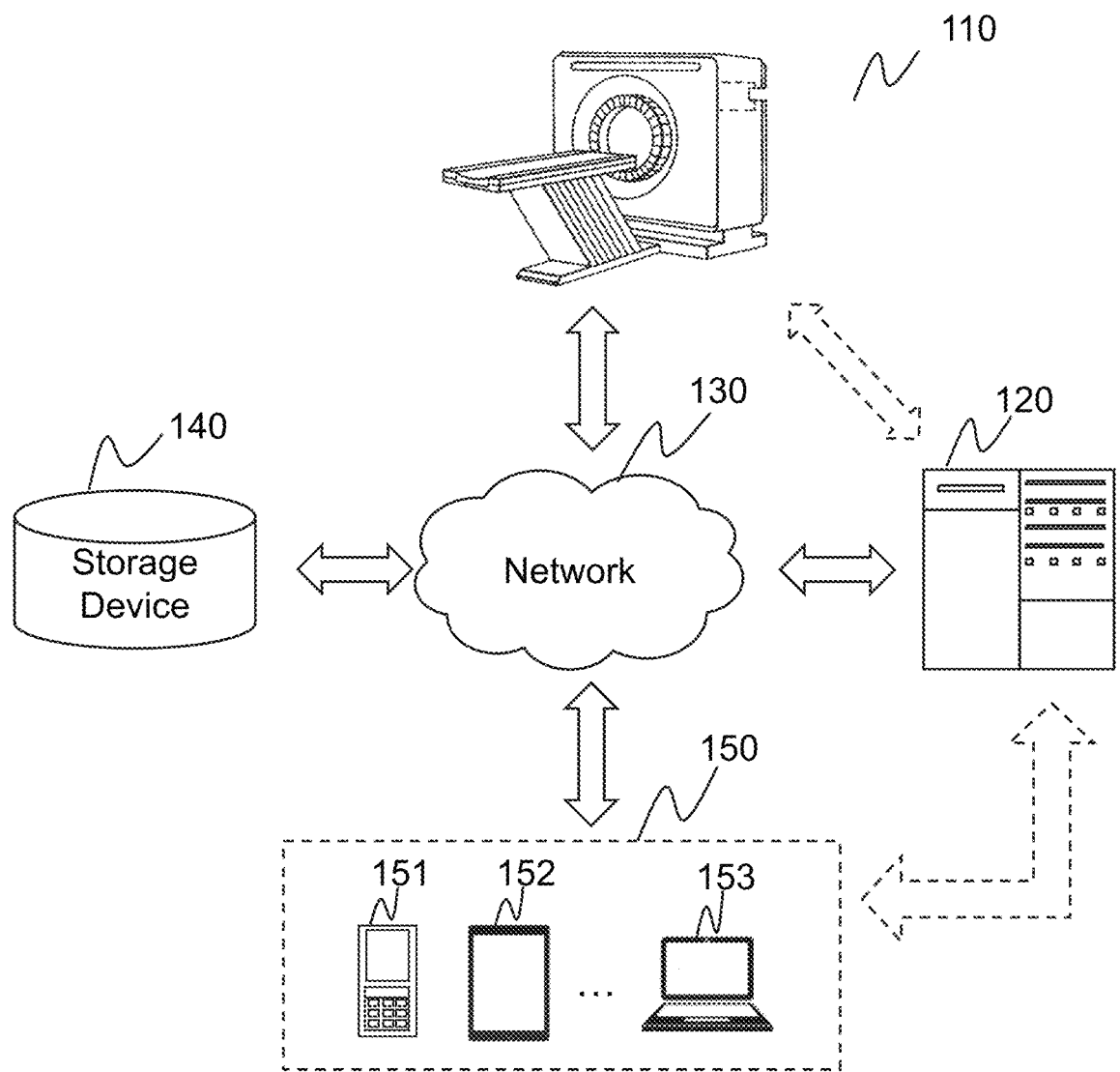
FIG. 1 is a block diagram illustrating an exemplary radiation therapy system according to some embodiments of the present disclosure.

FIG. 1 is a block diagram illustrating an exemplary radiation therapy system according to some embodiments of the present disclosure. In some embodiments, radiation therapy system 100 may be a multi-modality system including, for example, a positron emission tomography-radiotherapy (PET-RT) system, a magnetic resonance imaging-radiotherapy (MRI-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, one or more processing devices 120, a network 130, a storage device 140, and one or more terminal devices 150. In some embodiments, the therapeutic apparatus 110, the one or more processing devices 120, the storage device 140, and/or the terminal device 150 may be connected to and/or communicate with each other via a wireless connection (e.g., the wireless connection provided by the network 130), a wired connection (e.g., the wired connection provided by the network 130), or any combination thereof. In some embodiments, the therapeutic apparatus 110 may include an imaging device and a therapeutic device.

The therapeutic apparatus 110 may include a magnetic resonance imaging component (hereinafter referred to as "MRI device"). The MRI device may generate image data associated with magnetic resonance signals (hereinafter referred to as "MRI signals") via scanning a subject or a part of the subject. In some embodiments, the subject may include a body, a substance, an object, or the like, or any combination thereof. In some embodiments, the subject may include a specific portion of a body, a specific organ, or a specific tissue, such as head, brain, neck, body, shoulder, arm, thorax, heart, stomach, blood vessel, soft tissue, knee, feet, or the like, or any combination thereof. In some embodiments, the therapeutic apparatus 110 may transmit the image data via the network 130 to the one or more processing devices 120, the storage device 140, and/or the terminal device 150 for further processing. For example, the image data may be sent to the one or more processing devices 120 for generating an MRI image, or may be stored in the storage device 140.

The therapeutic apparatus 110 may also include a radiation therapy component (hereinafter referred to as "radiation therapy device"). The radiation therapy device may provide radiation for target region (e.g., a tumor) treatment. The radiation used herein may include a particle ray, a photon ray, etc. The particle ray may include neutron, proton, electron, μ-meson, heavy ion, α-ray, or the like, or any combination thereof. The photon ray may include X-ray, γ-ray, ultraviolet, laser, or the like, or any combination thereof. For illustration purposes, a radiation therapy device associated with X-ray may be described as an example. In some embodiments, the therapeutic apparatus 110 may generate a certain dose of X-rays to perform radiotherapy under the assistance of the image data provided by the MRI device. For example, the image data may be processed to locate a tumor and/or determine the dose of X-rays.

The one or more processing devices 120 may process data and/or information obtained from the therapeutic apparatus 110, the storage device 140, and/or the terminal device 150. For example, the one or more processing devices 120 may process image data and reconstruct at least one MRI image based on the image data. As another example, the one or more processing devices 120 may determine the position of the treatment region and the dose of radiation based on the at least one MRI image. The MRI image may provide advantages including, for example, superior soft-tissue contrast, high resolution, geometric accuracy, which may allow accurate positioning of the treatment region. The MRI image may be used to detect a change of the treatment region (e.g., tumor regression or metastasis) between when the treatment plan is determined and when the treatment is carried out, such that an original treatment plan may be adjusted accordingly. The original treatment plan may be determined before the treatment commences. For instance, the original treatment plan may be determined at least one day, or three days, or a week, or two weeks, or a month, etc., before the treatment commences.

In the original or adjusted treatment plan, the dose of radiation may be determined according to, for example, synthetic electron density information. In some embodiments, the synthetic electron density information may be generated based on the MRI image.

In some embodiments, the one or more processing devices 120 may be a single processing device that communicates with and process data from the MRI device and the radiation therapy device of the therapeutic apparatus 110. Alternatively, the one or more processing devices 120 may include at least two processing devices. One of the at least two processing devices may communicate with and process data from the MRI device of the therapeutic apparatus 110, and another one of the at least two processing devices may communicate with and process data from the radiation therapy device of the therapeutic apparatus 110. In some embodiments, the one or more processing devices 120 may include a treatment planning system. The at least two processing engines may communicate with each other.

In some embodiments, the one or more processing devices 120 may be a single server or a server group. The server group may be centralized or distributed. In some embodiments, the one or more processing devices 120 may be local to or remote from the therapeutic apparatus 110. For example, the one or more processing devices 120 may access information and/or data from the therapeutic apparatus 110, the storage device 140, and/or the terminal device 150 via the network 130. As another example, the one or more processing devices 120 may be directly connected to the therapeutic apparatus 110 as illustrated by the bidirectional arrow in dotted lines connection the processing device 120 and the therapeutic apparatus 110 in FIG. 1, the terminal device 150 as illustrated by the bidirectional arrow in dotted lines connection the processing device 120 and the terminal device 150 in FIG. 1, and/or the storage device 140 to access information and/or data. In some embodiments, the one or more processing devices 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the one or more processing devices 120, the storage device 140, or the terminal device 150) may communicate information and/or data with one or more other components of the radiation therapy system 100 via the network 130. For example, the one or more processing devices 120 may obtain image data from the therapeutic apparatus 110 via the network 130. As another example, the one or more processing devices 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the one or more processing devices 120 and/or the terminal device 150. In some embodiments, the storage device 140 may store data and/or instructions that the one or more processing devices 120 may execute or use to perform exemplary methods described in the present disclosure. In some embodiments, the storage device 140 may include a mass storage device, a removable storage device, a cloud-based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the one or more processing devices 120 or the terminal device 150). One or more components of the radiation therapy system 100 may access the data or instructions stored in the storage device 140 via the network 130. In some embodiments, the storage device 140 may be part of the one or more processing devices 120.

The terminal device 150 may be connected to and/or communicate with the therapeutic apparatus 110, the one or more processing devices 120, and/or the storage device 140. For example, the one or more processing devices 120 may acquire a scanning protocol from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistant (PDA), a gaming device, a navigation device, a point of sale (POS) device, a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the one or more processing devices 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the one or more processing devices 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the one or more processing devices 120 may be integrated into the therapeutic apparatus 110. However, those variations and modifications do not depart the scope of the present disclosure.

FIG. 2 is a flowchart of an exemplary process 200 for applying therapeutic radiation by a radiation therapy system according to some embodiments of the present disclosure. In some embodiments, one or more operations of the process 200 illustrated in FIG. 2 may be implemented in the radiation therapy system 100 illustrated in FIG. 1. For example, the process 200 illustrated in FIG. 2 may be stored in the storage device 140 in the form of instructions, and invoked and/or executed by the one or more processing devices 120 illustrated in FIG. 1. For illustration purposes, the implement of the process 200 in the one or more processing devices 120 is described herein as an example. It shall be noted that the process 200 can also be similarly implemented in the terminal device 150.

In 202, the one or more processing devices 120 may acquire magnetic resonance imaging (MRI) data with respect to a region of interest (ROI) by an MRI device. The MRI data may be MR signals received by an RF coil from a subject. More detailed description related to the MR signals may be found elsewhere in the present disclosure at, for example, FIG. 3 and the description thereof.

In some embodiments, an ROI may refer to a treatment region associated with a lesion (e.g., a tumor). The treatment region may be a region of a subject (e.g., a body, a substance, an object). In some embodiments, the ROI may be a specific portion of a body, a specific organ, or a specific tissue, such as head, brain, neck, body, shoulder, arm, thorax, cardiac, stomach, blood vessel, soft tissue, knee, feet, or the like, or any combination thereof.

In 204, the one or more processing devices 120 may reconstruct an MRI image related to at least one portion of the ROI based on the MRI data. The MRI image may be reconstructed illustrating a distribution of atomic nuclei inside the subject based on the MRI data. Different kinds of imaging reconstruction techniques for the image reconstruction procedure may be employed. Exemplary image reconstruction techniques may include Fourier reconstruction, constrained image reconstruction, regularized image reconstruction in parallel MRI, or the like, or a variation thereof, or any combination thereof.

The MRI image may be used to determine therapeutic radiation to the lesion (e.g., the tumor). For example, the one or more processing devices 120 may determine the position of the tumor and the dose of radiation according to the MRI image. In some embodiments, it may take at least several minutes to reconstruct an MRI image representing a large imaging region. In some embodiments, in order to generate the MRI image during a relatively short time period (e.g., every second), the one or more processing devices 120 may reconstruct an initial image representing a smaller imaging region (e.g., at least one portion of the ROI) as opposed to the MRI image representing a large imaging region, and then combine the initial image with the MRI image representing a large imaging region. For example, the one or more processing devices 120 may replace a portion of the MRI image representing a large imaging region related to the ROI with the initial image. The MRI image representing a large imaging region may include information of non-ROI (e.g., a healthy tissue) near the ROI and that of the ROI. In some embodiments, the MRI image representing a large imaging region may be acquired and reconstructed before a session of the radiotherapy starts. For example, the MRI image representing a large imaging region may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before the radiation source starts emitting a radiation beam for treatment. In some embodiments, the MRI image representing a large imaging region may be obtained from a storage device in the radiation therapy system 100, such as the storage device 140.

In 206, the one or more processing devices 120 may determine a parameter associated with a size of the at least one portion of the ROI based on the MRI image. In some embodiments, the parameter associated with a size of the at least one portion of the ROI may include the size of a characteristic cross section of a lesion (e.g., a tumor) and is perpendicular to the direction of the radiation beams impinging on the at least one portion of the ROI. As used herein, a characteristic cross section of a lesion may be a cross section of the lesion, among cross sections of the lesion that are parallel to each other, whose area is the largest. In some embodiments, the ROI or a portion thereof may substantially conform to the characteristic cross section of the lesion. For instance, for an ROI having the shape of a circle, the diameter of the ROI may be the same as or slightly (e.g., no more than 5%, or 10%, or 15%, or 20%, or 25%, or 30%, or 40%, or 50%) larger than the largest dimension of the characteristic cross section of the lesion. As another example, for an ROI having the shape of an ellipse or a polygon (e.g., a square, a rectangle, etc.), the area of the ROI may be the same as or slightly (e.g., no more than 5%, or 10%, or 15%, or 20%, or 25%, or 30%, or 40%, or 50%) larger than the area of the characteristic cross section of the lesion.

In some embodiments, the parameter associated with a size of the at least one portion of the ROI may indicate the shape of the characteristic cross section of the tumor. For example, the parameter associated with a size of at least one portion of the ROI may indicate that the shape of the cross section of the tumor is a circle or an approximate circle, and further indicate the diameter of the circle or the approximate circle. In some embodiments, to determine the parameter associated with a size of at least one portion of the ROI, the one or more processing devices 120 may extract texture information from the MRI image, and determine texture features that are indicative of the ROI by identifying frequent texture patterns of the ROI in the extracted texture information. Then, the one or more processing devices 120 may measure the size of the region which includes the texture features in the MRI image, and determine the parameter associated with the size of the ROI.

In 208, the one or more processing devices 120 may generate a control signal according to the parameter associated with the size of at least one portion of the ROI. The control signal may be dynamically adjusted based on the plurality of MRI images taken at different time points (e.g., at a first radiation therapy session, at a second radiation therapy session, etc.). In some embodiments, the control signal may include parameters associated with the therapeutic radiation on the tumor. For example, the control signal may include the dosage of X-rays and a duration of the radiation beam. As another example, the control signal may include parameters of the multi-leaf collimator (MLC) that determines the shape of the radiation beam projected on the subject. The MLC may include a plurality of individual leaves of high atomic numbered materials (e.g., tungsten) moving in and out of the path of the radiation beam. The movement of some or all of the plurality of leaves may be independent from each other. In some embodiments, the control signal may include parameters associated with movements of one or more components of a radiation therapy device. For example, the control signal may include a parameter associated with one or more positions of a radiation source of the radiation therapy device (e.g., the radiation therapy device in the therapeutic apparatus 110, a radiation therapy device 300). As another example, the control signal may include a parameter associated with a height or a position of a platform of the radiation therapy apparatus (e.g., a location of the platform 308 of the treatment table 330 along an axis of the magnetic body 302) to properly position a patient so that the treatment region (e.g., a cancerous tumor) in the patient may properly receive the radiation beam from the radiation therapy device.

In 210, the one or more processing devices 120 may send the control signal to a radiation therapy device to cause the radiation therapy device to apply the therapeutic radiation. During a therapeutic radiation session, one or more components of the radiation therapy device may coordinate to deliver the therapeutic radiation. For instance, the radiation source (e.g., a linear accelerator) of the radiation therapy device may rotate; alternatively or additionally, the radiation therapy session may proceed according to a collection of parameters including, e.g., the dosage of X-rays, the duration of a radiation beam from a radiation source, the shape of the MLC, and the position of the platform, etc., that change over time cooperatively. In some embodiments, the radiation beam may be emitted only when the radiation source of the radiation therapy device rotates to certain angles (e.g., 60 degrees, 120 degrees, 180 degrees, 240 degrees, 300 degrees, 360 degrees). For example, an intensity modulated radiation therapy (IMRT) may be applied. The radiation source may stop rotating intermittently. The radiation source may rotate to a desired position, pause there, emit a radiation beam for a specific duration, and then resume to rotate. In some embodiments, the radiation source may rotate continuously, and emit a radiation beam continuously or intermittently. In some embodiments, the radiation source may continuously emit the radiation beam while rotating.

In some embodiments, as described above, a treatment region (e.g., a region including a tumor) may be determined according to the image data acquired from the MRI device. Then a radiation beam may be generated by a radiation source of the radiation therapy device to the treatment region by delivering the therapeutic radiation. For example, the dosage of the radiation beam and/or the position of the treatment region may be determined in real-time with the assistance of the MRI device.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 202 and 204 may be performed simultaneously.

Figure 3A:
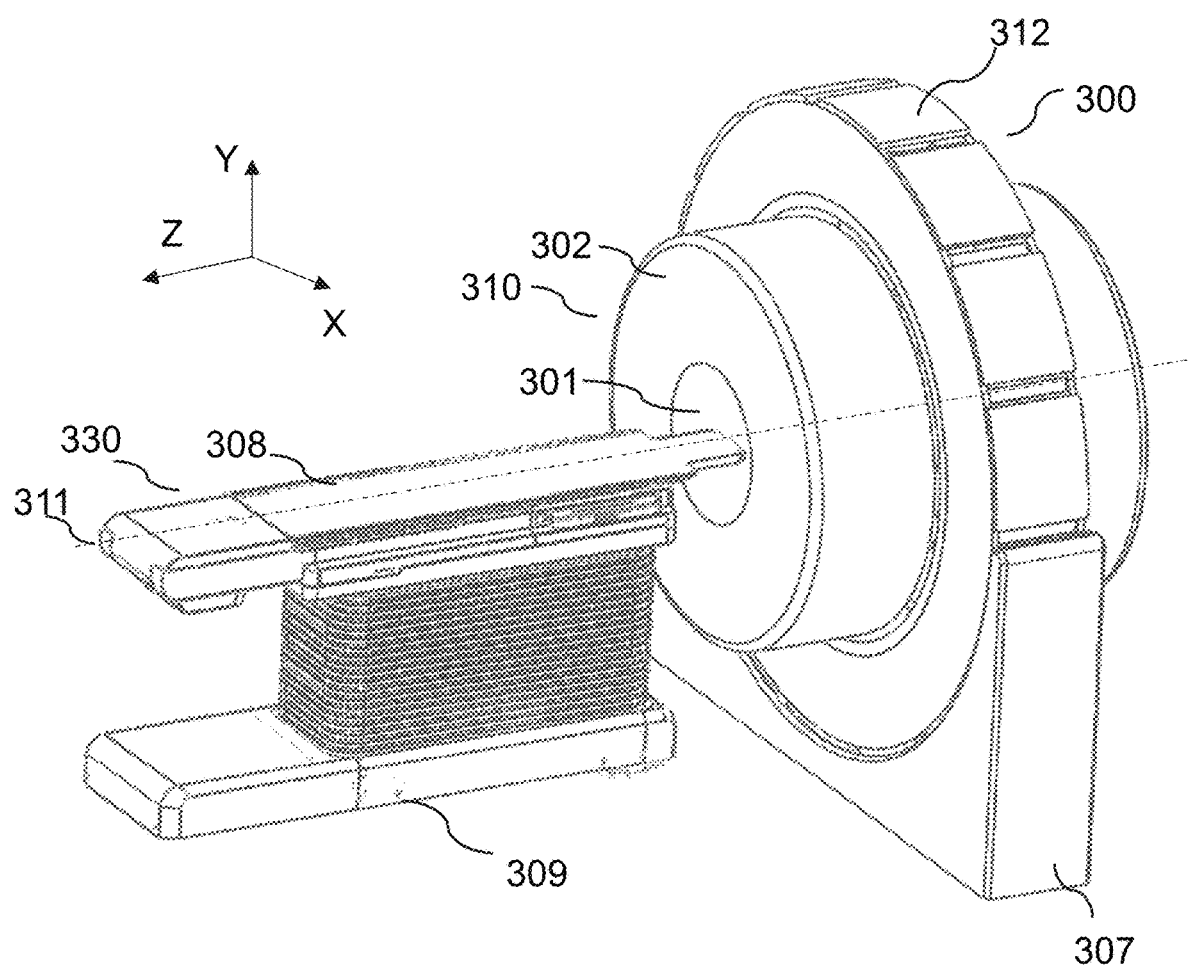
FIG. 3A illustrates an exemplary therapeutic apparatus according to some embodiments of the present disclosure.

FIG. 3A illustrates an exemplary therapeutic apparatus according to some embodiments of the present disclosure. As illustrated in FIG. 3A, the therapeutic apparatus 110 may include an MRI scanner 310, a radiation therapy device 300, and a treatment table 330. In some embodiments, the MRI scanner 310 may generate the MRI data as described in connection with operation 202, and the radiation therapy device 300 may apply the therapeutic radiation as described in connection with operation 210.

The MRI scanner 310 may include a bore 301, a magnetic body 302, one or more gradient coils (not shown), and one or more radiofrequency (RF) coils (not shown). The MRI scanner 310 may be configured to acquire image data from an imaging region. For example, the image data may relate to the treatment region associated with a tumor. In some embodiments, the MRI scanner 310 may be a permanent magnet MRI scanner, a superconducting electromagnet MRI scanner, or a resistive electromagnet MRI scanner, etc., according to the types of the magnetic body 302. In some embodiments, the MRI scanner 310 may be a high-field MRI scanner, a mid-field MRI scanner, and a low-field MRI scanner, etc., according to the intensity of the magnetic field. In some embodiments, the MRI scanner 310 may be of a closed-bore (cylindrical) type, an open-bore type, or the like.

The magnetic body 302 may have the shape of an annulus and may generate a static magnetic field B0 (or a main magnetic field B0). In some embodiments, the magnetic body 302 may be housed in an cryostat (e.g., an annulus cryostat) containing a cooling medium (e.g., liquid helium). The magnetic body 302 may be of various types including, for example, a permanent magnet, a superconducting electromagnet, a resistive electromagnet, etc. The superconducting electromagnet may include one or more electrically conductive coils that are made of conductive materials, such as niobium, vanadium, technetium alloy, etc. For example, the superconducting electromagnet may be employed to generate the large magnetic fields which the MRI scanner 310 needs for operation. To realize superconductivity, the superconducting electromagnet may be maintained in a cryogenic environment at a temperature near absolute zero. The MRI scanner 310 may employ the cryostat containing some amount of a cooling medium (e.g., liquid helium). The superconducting electromagnet composed of the one or more electrically conductive coils that are disposed in the cryostat. The one or more electrically conductive coils may be configured to generate the main magnetic field B0 through electrical current circulating therein. The cryostat is not shown in FIG. 3A. Exemplary structures of the cryostat may be found elsewhere in the present disclosure (e.g., the cryostat 400, 400', 500, 500', 600 or 600' described below).

The one or more gradient coils may be employed to generate magnetic field gradients to the main magnetic field B0 in the X, Y, and/or Z directions (or axes). In some embodiments, the one or more gradient coils may include an X-direction (or axis) coil, a Y-direction (or axis) coil, a Z-direction (or axis) coil, etc. For example, the Z-direction coil may be designed based on a circular (Maxwell) coil, the X-direction coil and the Y-direction coil may be designed on the basis of the saddle (Golay) coil configuration. As used herein, the X direction may also be referred to as the readout (RO) direction (or a frequency encoding direction), the Y direction may also be referred to as the phase encoding (PE) direction, the Z direction may also be referred to as the slice-selection encoding direction. In the present disclosure, the readout direction and the frequency encoding direction may be used interchangeably.

Merely by way of example, the gradient magnetic fields may include a slice-selection gradient field corresponding to the Z-direction, a phase encoding (PE) gradient field corresponding to the Y-direction, a readout (RO) gradient field corresponding to the X-direction, etc. The gradient magnetic fields in different directions may be used to encode the spatial information of MR signals. In some embodiments, the gradient magnetic fields may also be used to perform at least one function of flow encoding, flow compensation, flow dephasing, or the like, or any combination thereof.

The one or more RF coils may emit RF pulses to and/or receive MR signals from a subject (e.g., a body, a substance, an object) being examined. As used herein, an RF pulse may include an excitation RF pulse and a refocusing RF pulse. In some embodiments, the excitation RF pulse (e.g., a 90-degree RF pulse) may tip magnetization vector away from the direction of the main magnetic field B0. In some embodiments, the refocusing pulse (e.g., a 180-degree RF pulse) may rotate dispersing spin isochromatic about an axis in the transverse plane so that magnetization vector may rephase at a later time. In some embodiments, the RF coil may include an RF transmitting coil and an RF receiving coil. The RF transmitting coil may emit RF pulse signals that may excite the nucleus in the subject to resonate at the Larmor frequency. The RF receiving coil may receive MR signals emitted from the subject. In some embodiments, the RF transmitting coil and RF receiving coil may be integrated into one single coil, for example, a transmitting/receiving coil. The RF coil may be one of various types including, for example, a quotient difference (QD) orthogonal coil, a phase-array coil, etc. In some embodiments, different RF coils 240 may be used for the scanning of different parts of a body being examined, for example, a head coil, a knee joint coil, a cervical vertebra coil, a thoracic vertebra coil, a temporomandibular joint (TMJ) coil, etc. In some embodiments, according to its function and/or size, the RF coil may be classified as a volume coil and a local coil. For example, the volume coil may include a birdcage coil, a transverse electromagnetic coil, a surface coil, etc. As another example, the local coil may include a solenoid coil, a saddle coil, a flexible coil, etc.

The radiation therapy device 300 may include a drum 312 and a pedestal 307. The drum 312 may have the shape of an annulus. The drum 312 may be disposed around the magnetic body 302 and intersect the magnetic body 302 at a central region of the magnetic body 302 along the axis 311 of the bore 301. The drum 312 may accommodate and support a radiation source that is configured to emit a radiation beam towards the treatment region in the bore 301. The radiation beam may be an X-ray beam, an electron beam, a gamma ray source, a proton ray source, etc. The drum 312, together with the radiation source mounted thereon, may rotate around the axis 311 of the bore 301 and/or a point called the isocenter. Merely by way of example, the drum 312, together with the radiation source mounted thereon, may rotate any angle, e.g., 90 degrees, 180 degrees, 360 degrees, 450 degrees, 540 degrees, around the axis 311. The drum 312 may be further supported by the pedestal 307.

It should be noted that the above description is merely provided for the purposes of illustration, and not intended to limit the scope of the present disclosure. For persons having ordinary skills in the art, multiple variations or modification may be made under the teaching of the present disclosure. For example, the radiation therapy device 300 may further include a linear accelerator configured to accelerate electrons, ions, or protons, a dose detecting device, a temperature controlling device (e.g., a cooling device), a multiple layer collimator, or the like, or any combination thereof. However, those variations and modifications do not depart from the scope of the present disclosure.

The treatment table 330 may include a platform 308 and a base frame 309. In some embodiments, the platform 308 may move along the horizontal direction and enter into the bore 301 of the MRI scanner 310. In some embodiments, the platform 308 may move two-dimensionally, or three-dimensionally. In some embodiments, the platform 308 may move to compensate the variance (e.g., position change) of the tumor estimated by, for example, a real-time MRI image obtained during a treatment.

In some embodiments, the subject may be placed on the platform 308 and sent into the MRI device. In some embodiments, the subject may be a human patient. The human patient may lie on the back, in prone, on the side of the platform 308, etc.

During the treatment, the drum 312 may be set to rotate around the magnetic body 302. In some embodiments, the magnetic body 302 may include a recess (not shown) at its outer wall. The recess may be disposed around the entire circumference of the magnetic body 302. For example, the recess may have the shape of an annulus surrounding the magnetic body 302, thus accommodating at least part of the drum 312. In some embodiments, the recess may be disposed around part of the circumference of the magnetic body 302. For example, the recess may have the shape of one or more arcs around the magnetic body 302.

In some embodiments, the radiation source may move along an entire path of rotation within the recess. The radiation source may generate the radiation beam according to one or more parameters. Exemplary parameters may include a parameter of the radiation beam, a parameter of the radiation source, a parameter of the platform 308, or the like, or a combination thereof. For example, the parameter of the radiation beam may include an irradiating intensity, an irradiating angle, an irradiating distance, an irradiating area, an irradiating time, an intensity distribution, or the like, or any combination thereof. The parameter of the radiation source may include a position, a rotating angle, a rotating speed, a rotating direction, the configuration of the radiation source, or the like, or any combination thereof. In some embodiments, the generation of the radiation beam by the radiation source may take into consideration energy loss of the radiation beam due to, e.g., the magnetic body 302 located in the pathway of the radiation beam that may absorb at least a portion of the radiation beam. For example, the irradiating intensity of the radiation beam may be set larger than that in the situation in which there is no energy loss due to, e.g., the absorption by the magnetic body 302 accordingly to compensate the energy loss such that the radiation beam of a specific intensity may impinge on a treatment region (e.g., a tumor).

Figure 3B:
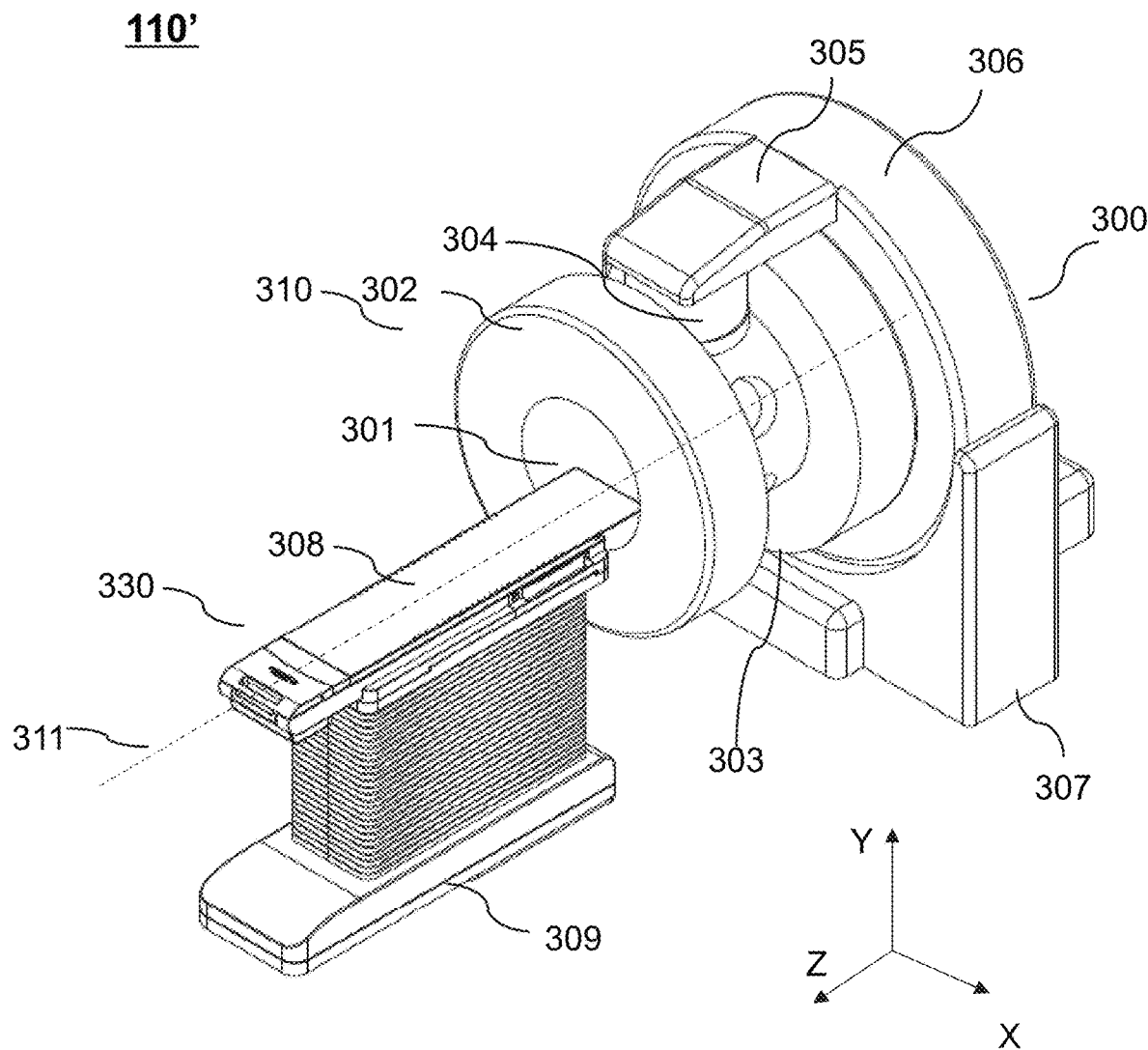
FIG. 3B illustrates another exemplary therapeutic apparatus according to some embodiments of the present disclosure.

FIG. 3B illustrates another exemplary therapeutic apparatus according to some embodiments of the present disclosure. Compared with the therapeutic apparatus 110 described in FIG. 3A, therapeutic apparatus 110' may use a gantry 306 instead of the drum 312. The gantry 306 may be disposed at one side of the magnetic body 302. A treatment head 304 may be installed on the gantry 306 via a treatment arm 305. The treatment head 304 may accommodate the radiation source (e.g., a linear accelerator). The gantry 306 may be able to rotate the treatment head 304 around the axis 311 of the bore 301.

As shown in FIG. 3B, a recess 303 may be formed at the outer wall of the magnetic body 302 and have the shape of an annulus. The recess 303 may accommodate at least a portion of the treatment head 304 and provide a path for rotation of the treatment head 304. This arrangement may reduce the distance between the treatment head 304 and the axis 311 of the bore 301 along the radial direction of the magnetic body 302. In some embodiments, the reduction of the distance between the treatment head 304 and the axis 311 of the bore 301 may cause an increase of the radiation dose that may reach the treatment region (e.g., a tumor) which leads to an enhancement in the therapeutic efficiency. In some embodiments, the width of the recess 303 along the Z direction (i.e., the axial direction of the magnetic body 302) may be no less than the width of the treatment head 304 along the Z direction.

It should be noted that the above description of the therapeutic apparatus 110 is merely provided for the purposes of illustration, and not intended to limit the scope of the present disclosure. For persons having ordinary skills in the art, multiple variations and modifications may be made under the teachings of the present disclosure. For example, the assembly and/or function of the therapeutic apparatus 110 may vary or change according to a specific implementation scenario. In some embodiments, the magnetic body 302 of the MRI scanner 310 may also rotate relative to the treatment head 304. For example, the radiation therapy device 300 and the MRI scanner 310 may synchronously or asynchronously rotate around the same axis (e.g., the axis 311). However, those variations and modifications do not depart from the scope of the present disclosure.

Figure 4A:
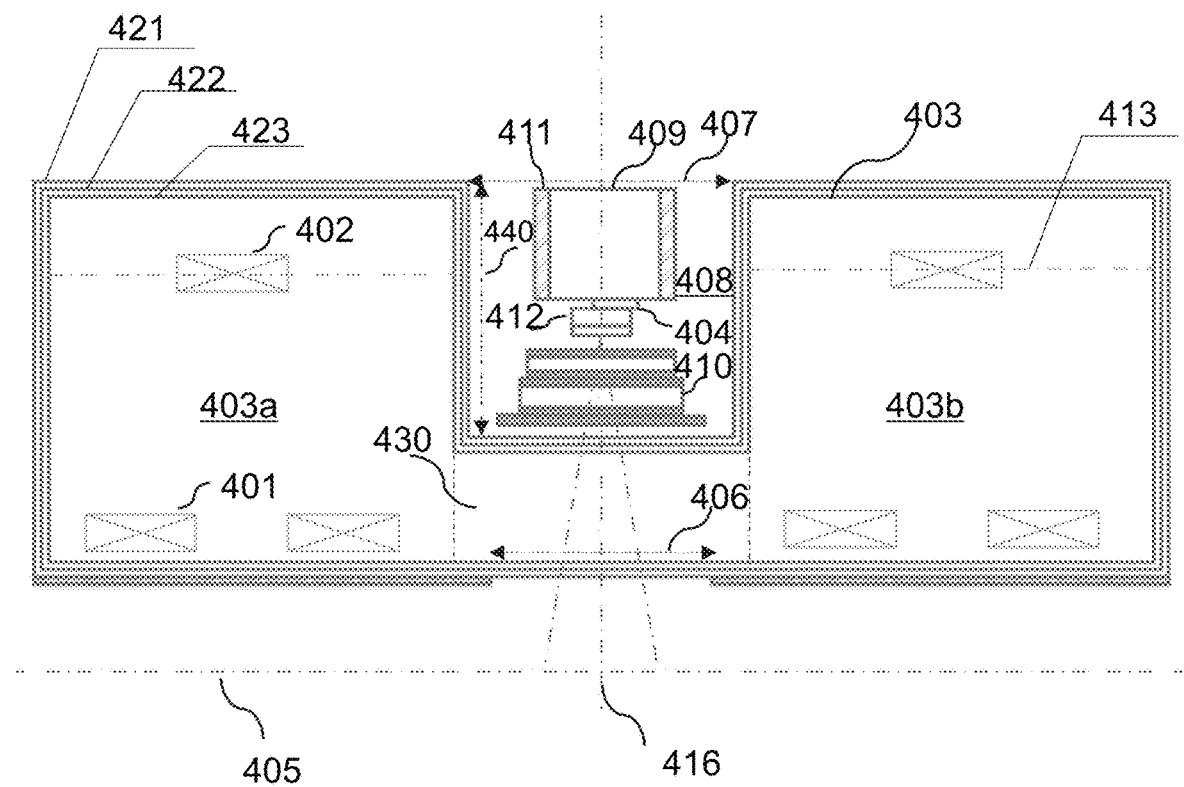
FIG. 4A shows a cross-sectional view of an upper portion of an exemplary therapeutic apparatus viewed along the X direction according to some embodiments of the present disclosure.

FIG. 4A shows a cross-sectional view of an upper portion of an exemplary therapeutic apparatus viewed along the X direction according to some embodiments of the present disclosure. Therapeutic apparatus 400 may include an MRI device (e.g., MRI scanner 310) that is configured to generate MRI data and a radiation therapy device (e.g., radiation therapy device 300) that is configured to apply therapeutic radiation. As shown in FIG. 4A, the MRI device may include a plurality of main magnetic coils 401, a plurality of shielding magnetic coils 402, and a cryostat 403.

The plurality of main magnetic coils 401 and the plurality of shielding magnetic coils 402 may be accommodated in the cryostat 403 and maintained in the superconductive state under a certain condition (e.g., when both the coils are merged in a cooling medium in the cryostat 403).

In some embodiments, the cryostat 403 may have the shape of an annulus with an axis 405 (e.g., the axis 311 in FIG. 3A). The plurality of main magnetic coils 401 may be arranged coaxially along the axis 405 to generate a uniform magnetic field (e.g., a static magnetic field B0) within a specific region (e.g., the region within the bore 301) when the plurality of main magnetic coils 401 carry an electric current along a first direction.

The plurality of shielding magnetic coils 402 may also be arranged coaxially along the axis 405 at a larger radius from the axis 405 than the plurality of main magnetic coils 401. The plurality of shielding magnetic coils 402 may carry an electric current along a second direction that is opposed to the first direction. The plurality of shielding magnetic coils 402 may be configured to shield the magnetic field generated by the plurality of main magnetic coils 401 on a region outside the MRI apparatus.

In some embodiments, the cryostat 403 may include one or more chambers enclosed by an annular structure arrangement. For example, the annular structure arrangement may include multiple annular structures, such as a first annular structure 421, a second annular structure 422, and a third annular structure 423. Merely for illustration, the cryostat 403 may include two chambers (e.g., a first chamber 403a and a second chamber 403b) as shown in FIG. 4A. The two chambers may be located on opposite sides of the cryostat 403 along the axial direction (i.e., the direction of the axis 405) and may be connected by a neck portion 430 between the two chambers. The neck portion 430 may have a smaller radial size than the two chambers. In some embodiments, each chamber may have the shape of an annulus with a different outer wall. The outer wall may refer to the outer surface of the first annular structure 421 that has the shape of a ring, such as outer surface 721a of the first annular structure shown in FIG. 7. The two chambers and the neck portion may share a same inner wall, i.e., the inner wall of the cryostat 403. In some embodiments, the inner wall may refer to the inner surface of the first annular structure 421 that has the shape of a ring, such as inner surface 721b of the first annular structure shown in FIG. 7. In some embodiments, a bore (e.g., the bore 301 of the MRI scanner 310) of the MRI device may include a region surrounded by the inner wall of the cryostat. In some embodiments, each chamber may accommodate at least one of the plurality of main magnetic coils 401 and at least one of the plurality of shielding magnetic coils 402. For example, at least one of the plurality of main magnetic coils 401 may be arranged near the inner wall of the left chamber, and at least one of the plurality of shielding magnetic coils 402 may be arranged near the outer wall of the left chamber. A gap 406 may be formed between the main magnetic coils arranged in the first chamber 403a and the main magnetic coils arranged in the second chamber 403b, allowing the radiation beam produced by the radiation therapy apparatus to pass through. The two chambers may be in fluid communication with each other through the neck portion between them. The cryostat 403 may contain a cooling medium in which the plurality of main magnetic coils 401 and the plurality of shielding magnetic coils 402 are merged to achieve the superconducting state. Exemplary cooling medium may be liquid helium. As shown in FIG. 4A, the plurality of main magnetic coils 401 and the plurality of shielding magnetic coils 402 are immersed below the liquid level 413 of the liquid helium.

Figure 7:
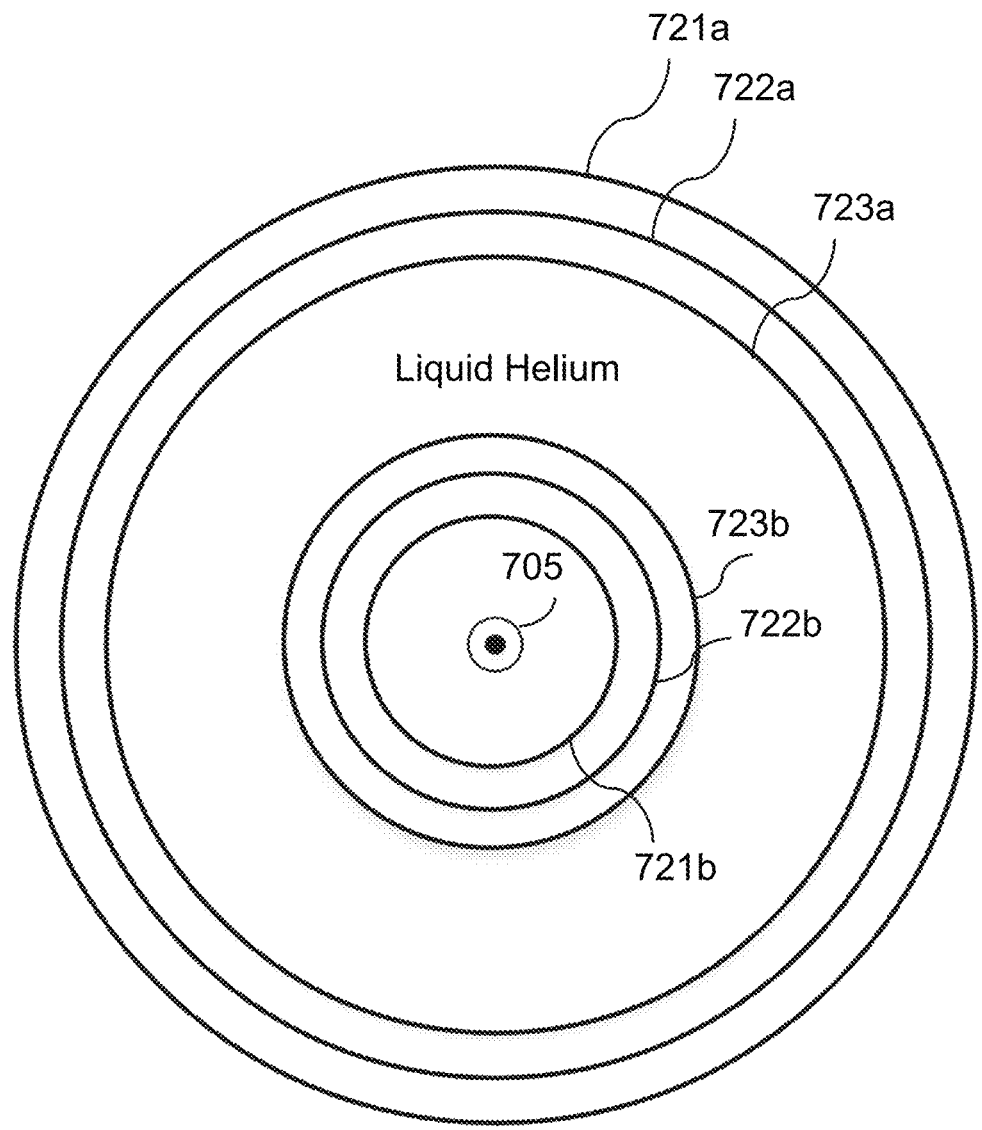
FIG. 7 shows a cross-sectional view of an exemplary cryostat viewed along an axial direction (i.e., the Z direction) of the cryostat according to some embodiments of the present disclosure.

In some embodiments, the multiple annular structures of the annular structure arrangement may be arranged along a radial direction of the cryostat. Referring to FIG. 7 which shows a cross-sectional view of an exemplary cryostat viewed along an axial direction (i.e., the Z direction) of the cryostat according to some embodiments of the present disclosure. It is noted that cryostat 700 may be the same as or similar to the cryostat described in various embodiments of the present disclosure, such as the cryostat 403, 503, 603. In some embodiments, the annular structure arrangement may be deemed as a tube-in-tube structure. For example, the first annular structure 421 encloses the second annular structure 422, and the second annular structure 422 encloses the third annular structure 423. The outer and inner surfaces of the first annular structure, the second annular structure, and the third annular structure may be arranged along the radial direction of the cryostat as shown in FIG. 7. For example, the outer surface 721a of the first annular structure, the outer surface 722a of the second annular structure, the outer surface 723a of the third annular structure, the inner surface 723b of the third annular structure, the inner surface 722b of the second annular structure, and the inner surface 721b of the first annular structure are arranged from outer to inner of the cryostat. In some embodiments, the annular space surrounded by the inner surface 721b may extend along the axial direction 705 of the cryostat to form the bore of the MRI device.

Referring back to FIG. 4A, the first annular structure 421 may refer to a vacuum vessel for providing a vacuum space enclosing the one or more chambers (e.g., the left chamber and the right chamber). The second annular structure 422 may refer to a thermal shield for reducing heat transfer from the first annular structure 421 to the third annular structure 423. The third annular structure 423 may refer to a cryogen vessel for containing the cooling medium (e.g., liquid helium) to cool the plurality of main magnetic coils 401 and the plurality of shielding magnetic coils 402. The thermal shield may be provided in the vacuum space between the cryogen vessel and the vacuum vessel. In some embodiments, the multiple annular structures each may be made of various materials in order to retain a structural strength of the cryostat 403 and reduce radiation interference. More details about the materials which are made of the multiple annular structures may be found elsewhere in the present disclosure (e.g., FIG. 4C and the descriptions thereof).

In some embodiments, an annular recess may be disposed on the annular structure arrangement. Each annular structure may have a corresponding recess. As shown in FIG. 4A, the cryostat 403 may have a recess 408 at a radial position between the inner wall of the cryostat 403 (e.g., the inner surface of the first annular structure 421) and the outer walls of the different chambers of the cryostat 403 (e.g., two parts of the outer surface of the first annular structure 421 corresponding to the first chamber and the second chamber, respectively). The recess 408 may have an opening 407 formed between the outer surfaces of the first annular structure 421 corresponding to the first chamber and the second chamber. In some embodiments, the recess 408 may have the shape of an annulus when viewed in a perspective view. The annulus may have the same or different widths (i.e., the size in the axial direction) at different radial positions or portions of the annulus. The recess 408 may have a depth 440 (i.e., the thickness of the annulus in the radial direction) which is defined as the distance from the opening 407 to the outermost surface of the neck portion of the cryostat 403 in the radial direction.

In some embodiments, the recess 408 may be configured to accommodate one or more components of the radiation therapy device. As shown in FIG. 4A, the recess 408 may accommodate a radiation source, e.g., a linear accelerator that includes an accelerator 409, a magnetic shielding structure 411, a primary collimator 412, a target 404 and a multi-leaf collimator (MLC) 410.

The accelerator 409 may be configured to accelerate charged particles or ions to a high energy. In some embodiments, the accelerator 409 may accelerate electrons using microwave technology. For example, the accelerator 409 may accelerate the electrons in an electron beam with energy group between 4 MeV to 22 MeV using RF electromagnetic waves.

The accelerator 409 may be mounted to a gantry or a drum (e.g., the gantry 306 or the drum 312) that is capable of rotating around the axis 405 and may enable the radiation beam to be emitted from an arbitrary circumferential position. As shown in FIG. 4A, the gantry or the drum may rotate to a first position where the accelerator 409 may be located above the axis 405. The accelerator 409 may include an accelerating waveguide (tube) whose axis is perpendicular to the axis 405. The accelerating waveguide (tube) may provide a linear path for accelerating the electrons along a beam path that is perpendicular to the axis 405.

The accelerator 409 may be at least partially surrounded by the magnetic shielding structure 411. In some embodiments, the magnetic shielding structure 411 may provide a cavity coaxial with the longitudinal axis of the tube of the accelerator 409, with at least one end being open to let through the radiation beam emitted from the accelerator 409. In some embodiments, the accelerator 409 may be surrounded or substantially surrounded by the magnetic shielding structure 411. The magnetic shielding structure 411 may have any configuration. For example, the magnetic shielding structure 411 may include a first plate located at one side of the accelerator 409 along the circumferential direction of the recess 408 and a second plate located at the opposite side of the accelerator 409 along the circumferential direction of the recess 408. The first plate and the second plate may be symmetrical to each other with respect to the axis of the accelerator 409. The first plate and the second plate may form an enclosing structure to surround and/or hold the accelerator 409. Each of the two plates may have a shape similar to the symbol " $\mathbb{I}$ ", which provides a continuous pathway along the axial direction of the cryostat 803 for the magnetic field to pass through. In that the two plates of the magnetic shielding structure 411 are made of high magnetic susceptibility and/or permeability materials, the magnetic field may be conducted by the two plates and kept from the region formed between them, thus achieving the magnetic shielding for the accelerator 409. It should be noted that the magnetic shielding structure 411 may be of any shapes provided that at least one end of the magnetic shielding structure 411 is open for the radiation beam emitted from the accelerator 409 to pass. More descriptions regarding the embodiments with respect to the magnetic shielding structure may be found in, e.g., International Application No. PCT/CN2018/115394.

In some embodiments, the magnetic shielding structure 411 may include a plurality of magnetic shielding layers. At least one of the plurality of magnetic shielding layers may be used to reduce the magnetic interference between one or more components of the MRI device and the radiation therapy device. For example, the magnetic shielding structure 411 may include a magnetic shielding layer configured to shield the magnetic field produced by the MRI device (e.g., the main magnetic coils, the shielding magnetic coils, the gradient coils) in case that the electrons may be influenced by the magnetic field.

Additionally, at least one of the plurality of magnetic shielding layers may be used to reduce the RF and/or microwave interference between one or more components of the MRI device and the radiation therapy device. For example, the magnetic shielding structure 411 may include an electromagnetic shielding layer configured to shield the RF signals produced by the MRI device (e.g., the RF coils) and the microwave produced by the radiation therapy device.

The plurality of magnetic shielding layers may be made of the same material and/or different materials. For example, both the electromagnetic shielding layer and the magnetic shielding layer may be made of a material of a high magnetic susceptibility and magnetic permeability (e.g., non-oriented silicon steel), or one of the electromagnetic shielding layer and the magnetic shielding layer is made of a material of a high electric conductivity and magnetic permeability. In some embodiments, the plurality of magnetic shielding layers may be magnetically and/or electrically isolated from each other. In some embodiments, the plurality of magnetic shielding layers may be made of a suitable dielectric material, such as air or plastic, between them.

Additionally or alternatively, at least one of the plurality of magnetic shielding layers may be used to protect one or more components of the MRI device from the radiation produced by the accelerator 409. For example, one magnetic shielding layer of the plurality of magnetic shielding layers may be made of a material that is able to absorb the radiation produced by the radiation beam of the accelerator 409. Exemplary materials able to absorb the radiation may include a material for absorbing photon rays and/or material for absorbing neutron rays. The materials for absorbing photon rays may include steel, aluminum, lead, tungsten, etc. The materials for absorbing neutron rays may include boron, graphite, etc. It should be noted that, in some embodiments, the magnetic shielding structure 411 may be made only with radiation absorbing material, without high magnetic susceptibility and permeability material. In this way, the magnetic shielding structure 411 may only provide radiation shielding for one or more components of the MRI device.

The target 404 may be configured to receive the accelerated charged particles or ions (e.g., an electron beam) to produce the radiation beam for the therapeutic radiation. For example, the electron beam may collide with the target 404 to generate high-energy X-rays according to the bremsstrahlung effect. In some embodiments, the target 404 may be located near the exit window of the accelerator 409 to receive the accelerated electron beam. In some embodiments, the target 404 may be made of materials including aluminum, copper, silver, tungsten, or the like, or any combination thereof. Alternatively, the target 404 may be made of composite materials including tungsten and copper, tungsten and silver, tungsten and aluminum, or the like, or any combination thereof.

The radiation beam from the target 404 may pass through an aperture formed in the primary collimator 412 to form a beam with a specific shape (e.g., cone beam).

Figure 6A:
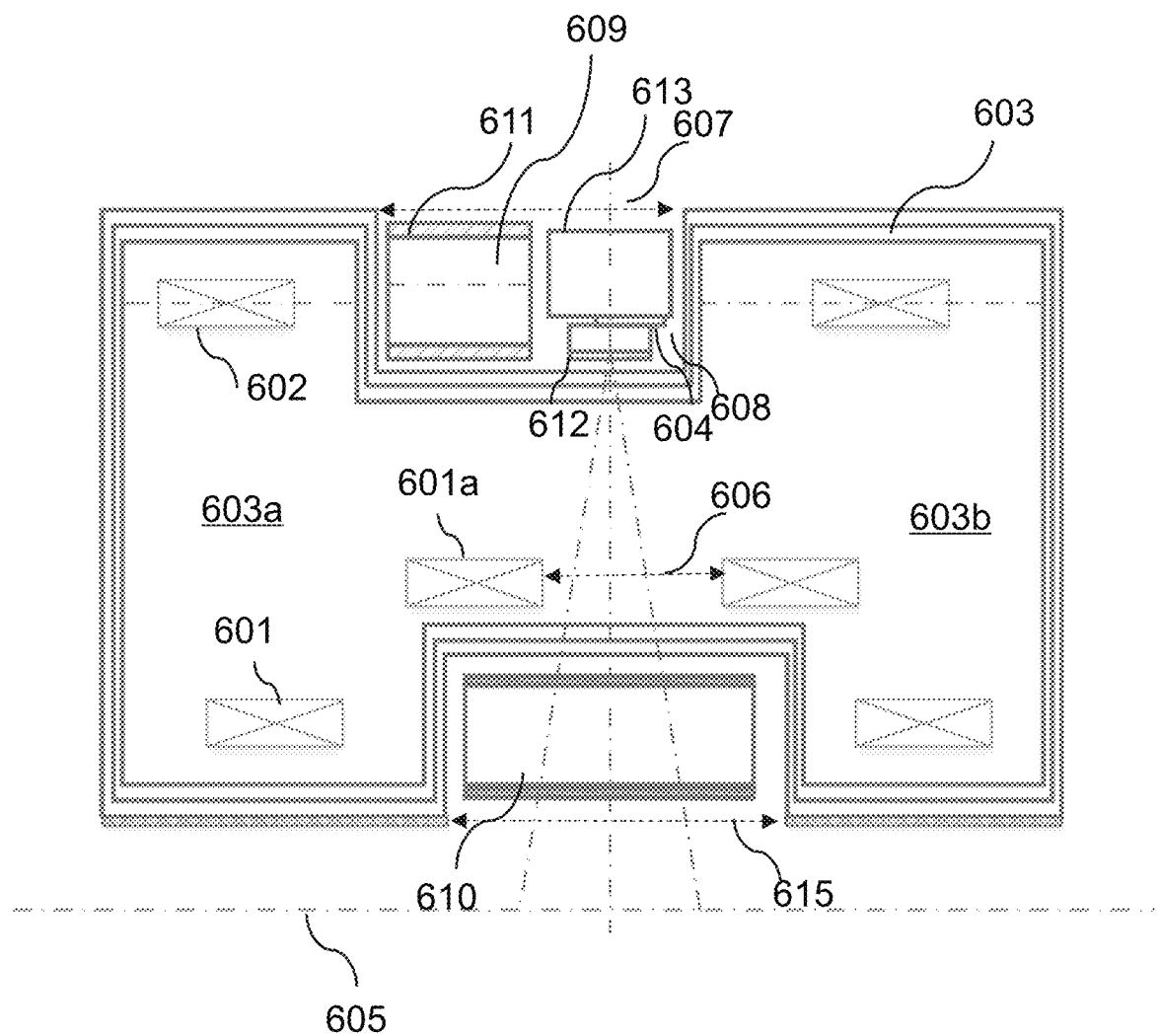
FIG. 6A shows a cross-sectional view of an upper portion of an exemplary therapeutic apparatus viewed along the X direction according to some embodiments of the present disclosure.

The MLC 410 may be configured to reshape the radiation beam. For example, the MLC 410 may adjust the irradiating shape, the irradiating area, etc., of the radiation beam. The MLC 410 may be placed anywhere on the path of the radiation beam. For example, the MLC 410 may be placed close to the accelerator 409 as shown in FIG. 4A. Thus, the radiation beam, after being reshaped by the MLC 410, may further pass through the neck portion of the cryostat 403 and the gap 406 between the plurality of main magnetic coils to arrive at the treatment region. As another example, the MLC 410 may be placed at a relatively long distance away from the accelerator (e.g., as shown in FIG. 6A) such that the MLC 410 may be closer to, e.g., the patient to be radiated.

The MLC 410 may remain fixed relative to the accelerator 409, thus rotating together with the accelerator 409 around the axis 405. The MLC 410 may include a plurality of individual leaves of high atomic numbered materials (e.g., tungsten) moving independently in and out of the path of the radiation beam in order to block it. The shape of the radiation beam may vary when the plurality of individual leaves move in and out, forming different slots that resemble the cross section of the tumor viewed from an axis of the radiation beam (i.e., the vertical dotted line 416 shown in FIG. 4A). In some embodiments, the MLC 410 may include one or more layers of leaves. For example, the MLC 410 may have only one layer of leaves and the height of the MLC 410 along the axis of the radiation beam may be between 7 and 10 centimeters. For another example, the MLC 410 may include two layers and the height of the MLC 410 may be at least 15 centimeters.

Figure 4B:
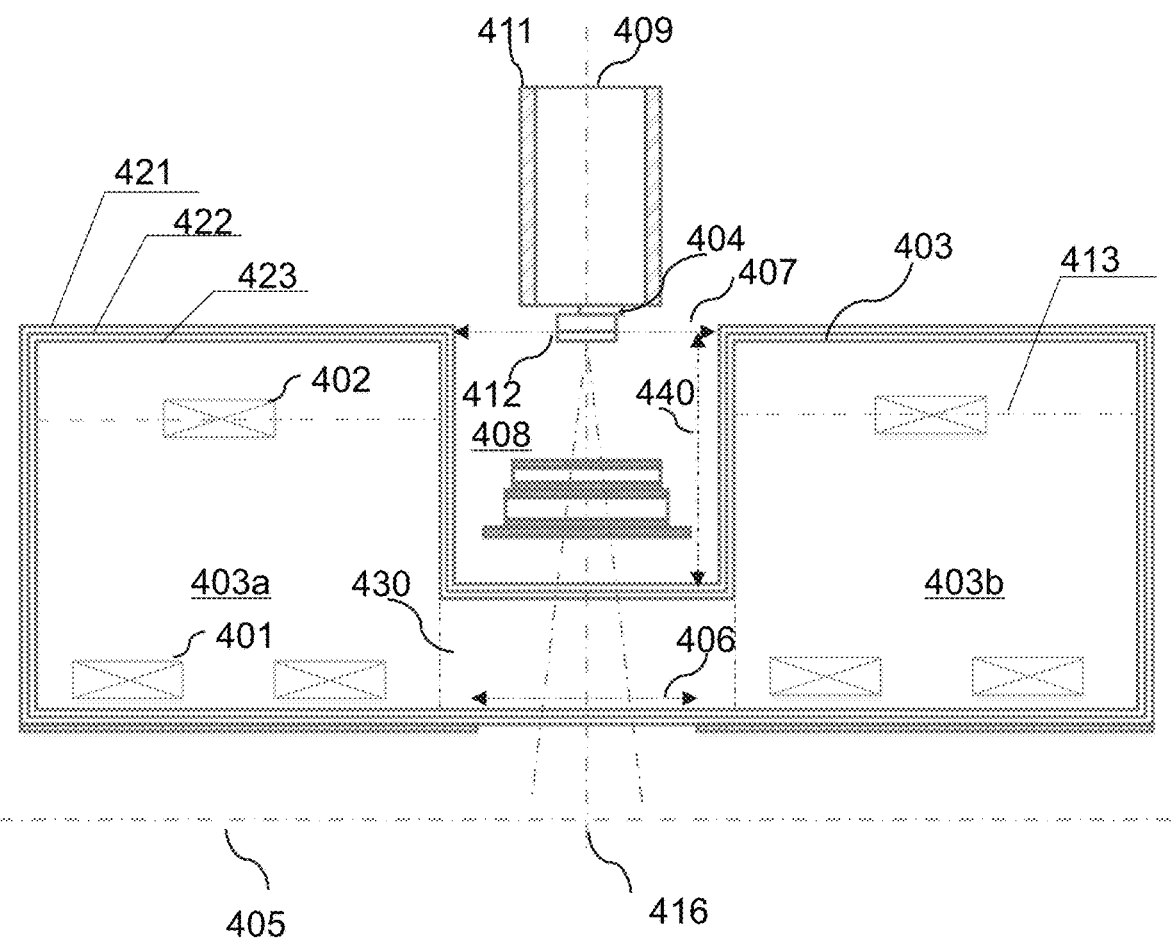
FIG. 4B shows a cross-sectional view of an upper portion of another exemplary therapeutic apparatus viewed along the X direction according to some embodiments of the present disclosure.

FIG. 4B shows a cross-sectional view of an upper portion of an exemplary therapeutic apparatus 400' viewed along the X direction according to some embodiments of the present disclosure. Compared with the therapeutic apparatus 400 described in FIG. 4A, at least part of the accelerator 409 of the therapeutic apparatus 400' may be located at the outside of the recess 408 along the radial direction of the cryostat 403. As shown in FIG. 4B, the accelerator 409 and the magnetic shielding structure 411 surrounding it along the axis of the radiation beam may stretch out of the opening 407 formed by the outer walls of the cryostat 403. In some embodiments, the accelerator 409 and the magnetic shielding structure 411 may be supported by or mounted to a gantry or a drum (e.g., the gantry 306 or the drum 312) that is capable of rotating around the axis 405.

Figure 4C:
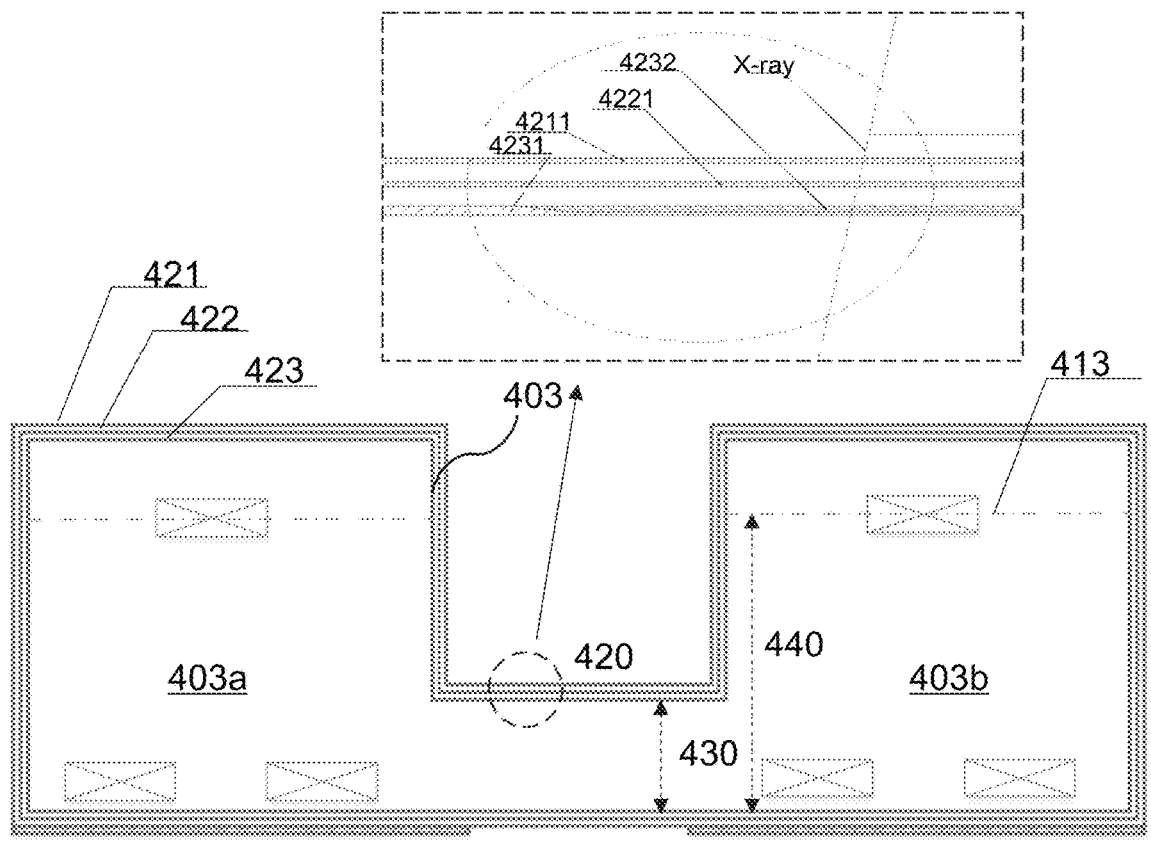
FIG. 4C shows a cross-sectional view of an upper portion of another exemplary cryostat viewed along the X direction according to some embodiments of the present disclosure.

FIG. 4C shows a cross-sectional view of an upper portion of an exemplary cryostat viewed along the X direction according to some embodiments of the present disclosure. As described in connection with FIG. 4A or FIG. 4B, two chambers of the cryostat 403 may be formed by the annular structure arrangement including the first annular structure 421, the second annular structure 422, and the third annular structure 423. In some embodiments, the first annular structure layer 421 may be the vacuum vessel, the second annular structure 422 may be the thermal shield, and the third annular structure 423 may be the cryogen vessel.

In radiotherapy using the radiation therapy device as described herein, before the radiation beam (e.g., high-energy X-rays) arrives at the treatment region (e.g., a lesion), the radiation beam may need to pass through the multiple annular structures of the cryostat 403 and the cooling medium (e.g., liquid helium) therein. During the passing through of the multiple annular structures, the radiation beam may be scattered, which may affect the dose rate of the radiotherapy. The extent of the effect may be assessed by a degree of scattering of the radiation beam. For example, if the degree of scattering is relatively big, a great decrease of the intensity of the radiation beam may occur. As a result, the lesion may not be effectively treated due to the weakened radiation energy than planned. It is desired to reduce the degree of scattering of the radiation beam by designing the structure of the cryostat 403.

The degree of scattering may depend on an effective thickness of the cryostat and/or a depth of the cooling medium contained in the one or more chambers of the cryostat. As used herein, an effective thickness is defined by a product of a physical thickness (i.e., an actual thickness) of an object and density thereof. On one hand, the degree of scatting may be reduced by decreasing the effective thickness of the cryostat compared to a conventional cryostat. On the other hand, the degree of the scatting may be reduced by controlling the depth of the cooling medium in the one or more chambers.

The effective thickness of the cryostat may be associated with the effective thickness of at least one of the multiple annular structures of the cryostat, such as the first annular structure 421, the second annular structure 422, and the third annular structure 423. The effective thickness may be determined based on the physical thickness(es) of the solid wall(s) of the annular structure and the density of the material(s) of each solid wall of the annular structure. For example, for an annular structure that has two solid walls made of a same material, the effective thickness ($L_{eff}$) of the annular structure may be equal to a product of the physical thickness (L) of two solid walls and the density (D) of the material of the solid walls, that is, $L_{eff}=L \times D$. As another example, if the cryostat has multiple annular structures that have N solid walls in total, each solid wall having a physical thickness of $L_i$ and made of a material whose density is $D_i$, the effective thickness ($L_{eff}$) may be equal to a sum of a product of the physical thickness ($L_i$) of the i-th solid wall and the density ($D_i$) of the material of the i-th solid wall, that is, $L_{eff}=\Sigma_1^N L_i \times D_i$. In some embodiments, under the premise of the structural strength of the cryostat, the effective thickness of at least one of the multiple annular structures may be designed to have a relatively small value by making the annular structure using one or more suitable materials. For example, at least one of the multiple annular structures may be made of a metallic material and a reinforcing material.

For most conventional cryostats, the multiple annular structures each may be made of only a same or different metallic materials, respectively. For example, the first annular structure 421 may be made of stainless steel, the second annular structure 422 may be made of aluminum, and the third annular structure 423 may be made of stainless steel. Due to the high density of the metallic materials used, the effective thickness of each of the annular structures becomes big as well. To effectively reduce the effective thickness of the annular structure and maintain the qualified structural strength, the annular structure may be made of different materials including a metallic material and a reinforcing material. The reinforcing material may be selected based on one or more characteristics of the material. The one or more characteristics may include a low density, a high mechanical strength, a radiation-resistance, a heat-resistance, or the like, or any combination thereof. Exemplary reinforcing materials may include a carbon fiber, a glass fiber, an aramid fiber, a silicon carbide (SiC) fiber, an asbestos fiber, a crystal whisker, a graphene fiber, an alloy material, and so on.

For example, the first annular structure 421 may be made of stainless steel and carbon fiber. The effective thickness of the first annular structure 421 may be smaller than a conventional first structure made of only stainless steel. As another example, the second annular structure 422 may be made of the aluminum and carbon fiber. The effective thickness of the second annular structure 422 may be smaller than a conventional second structure made of only aluminum. As a further example, the third annular structure 423 may be made of stainless steel and carbon fiber. The effective thickness of the third annular structure 423 may be smaller than a conventional third structure made of only the stainless steel. As described above, the effective thickness of the cryostat may be designed to have a relatively small value compared with a conventional cryostat. Thus, the degree of scattering may be reduced for a radiation beam to pass through the cryostat.

In some embodiments, because the first annular structure 421 and the second annular structure 422 are relatively thin compared with the third annular structure 423, little scattering of the radiation beam may occur. In some embodiments, the first annular structure 421 and the second annular structure 422 may be made of corresponding conventional metallic materials, while the third annular structure 423 may be made of the different materials. Merely for illustration, as shown in the enlarged structure diagram of a portion 420 of the annular structures of the cryostat 403 in FIG. 4C, the first annular structure 421 may be made of stainless steel 4221, the second annular structure 422 may be made of aluminum 4221, and the third annular structure 423 may be made of stainless steel 4231 and a reinforcing material 4232 (e.g., carbon fiber).

In some embodiments, when the radiation source (e.g., the linear accelerator) rotates at a specific angle, a radiation beam may traverse a nonuniform section of the cooling medium and be scattered. To resolve these or similar issues, the one or more chambers of the cryostat may be designed so that the radiation beam may always traverse a uniform section of the cooling medium when the radiation source rotates at various angles. As shown in FIG. 4C, the cryostat 403 may include the first chamber 403a and the second chamber 403b. The first chamber 403a and the second chamber 403b may be separated by the recessed neck portion of the cryostat (e.g., the neck portion 408 shown in FIG. 4A or 4B). The two chambers of the cryostat 403 may be equivalent to two sides of a communicating vessel, that is, the cryostat 403 may be equivalent to the communicating vessel. According to a theory of communicating vessel, the liquid level of the left chamber and the liquid level of the right chamber may be at the same level. When the liquid levels (e.g., the liquid level 413) of a cooling medium of the two chambers are higher than the height of neck portion of the cryostat 403, the neck portion may be filled with the cooling medium; there exists no part in the neck portion that is not filled with the cooling medium. The existence of a part in the neck portion that is not filled with the cooling medium may increase the degree of scattering of the radiation beam.

As shown in FIG. 4C, reference numeral 440 denotes a height of liquid level of the cooling medium, and reference numeral 430 denotes a height (e.g., a radial length) of the neck portion of the chamber of the cryostat 403. If it desires that the neck portion is filled with the cooling medium, the height 440 may always be greater than the height 430. In such case, a radiation beam may traverse the uniform the cooling medium when the radiation source rotates at various angles. Thus, the radiation beam having passed through the cryostat 403 may be relatively uniform. The radiotherapy quality may be improved accordingly. When the neck portion is filled with the cooling medium, the dose of the radiation beam as it passes through the cryostat may be guaranteed, which won't be affected by a rotation angle of the radiation source.

In some embodiments, one or more level sensors may be mounted on the cryostat 403. The one or more level sensors may be configured to detect the liquid level of the cooling medium of each chamber of the cryostat 403. For example, when the liquid level of the cooling medium is lower than a level limit, the processing device 120 may generate an alert for notifying a user (e.g., an operator) to inject the cooling medium to the cryostat 403 through a cold head (not shown in FIG. 4C). In some embodiments, the level limit may be a value greater than the height 430. In some embodiments, the one or more level sensors may include a sight glass liquid level sensor, an ultrasonic sensor, a laser sensor, an infrared sensor, or the like, or any combination thereof.

It should be noted that the above description of the therapeutic apparatus 400 or 400' is merely provided for the purposes of illustration, and not intended to limit the scope of the present disclosure. For persons having ordinary skills in the art, multiple variations and modifications may be made under the teachings of the present disclosure. For example, the primary collimator 412 and the MLC 410 may be integrated to form a single collimator. For another example, the neck portion illustrated in the cryostat 403 may not form an entire annulus. Specifically, the neck portion may be discrete arcs that connect the left chamber and the right chamber of the cryostat 403. Therefore, the neck portion may intermittently appear in the path of the radiation beam when the accelerator 409 rotates around the axis 405 to generate the radiation beam.

Figure 5A:
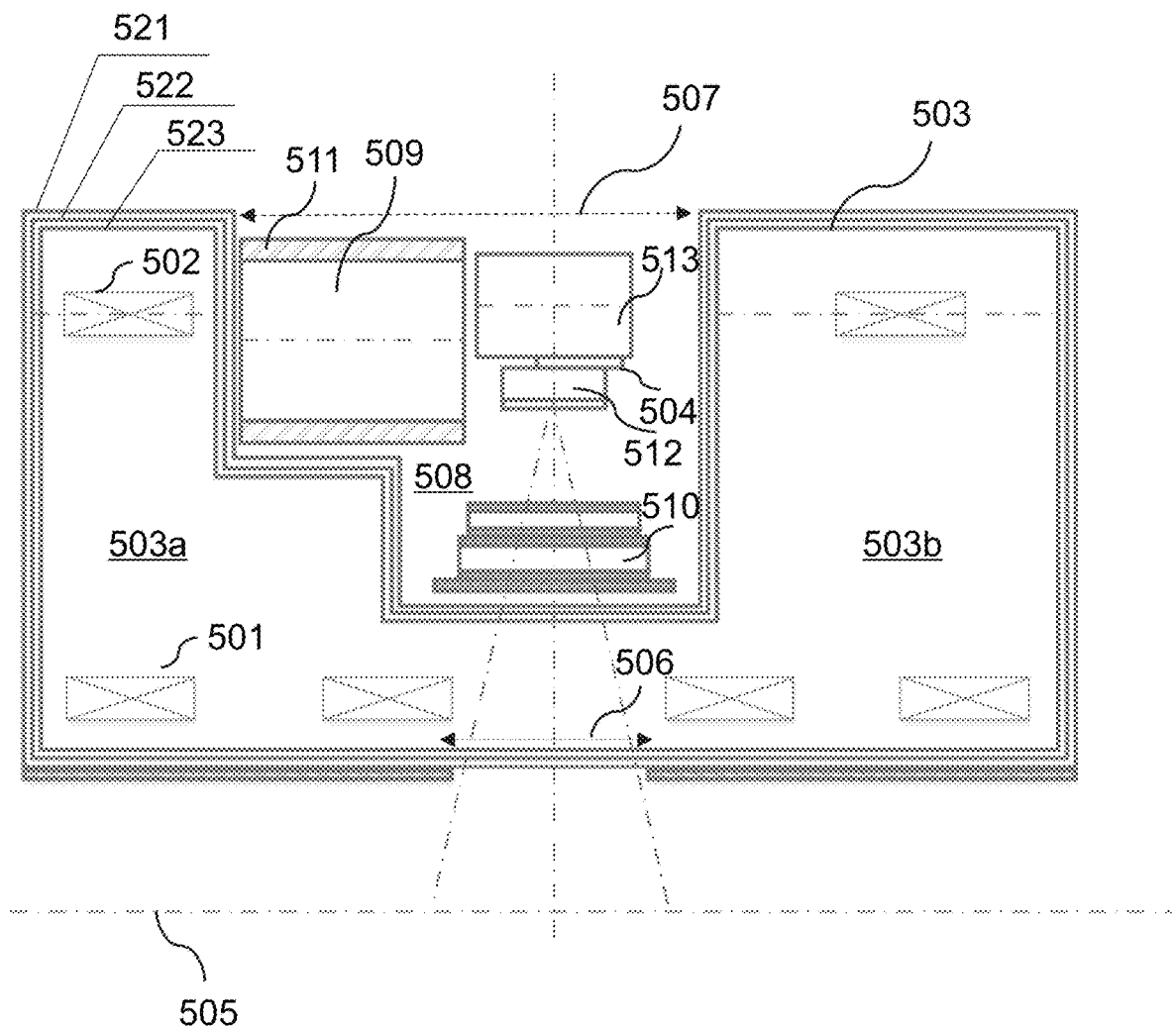
FIG. 5A shows a cross-sectional view of an upper portion of an exemplary therapeutic apparatus viewed along the X direction according to some embodiments of the present disclosure.

FIG. 5A shows a cross-sectional view of an upper portion of an exemplary therapeutic apparatus viewed along the X direction according to some embodiments of the present disclosure. As shown in FIG. 5A, the therapeutic apparatus 500 may include a plurality of main magnetic coils 501, a plurality of shielding magnetic coils 502, a cryostat 503 with an axis, a target 504, a gap 506, an opening 507, a recess 508, a accelerator 509, an MLC 510, a shielding structure 511, a primary collimator 512, and a deflection unit 513. The plurality of main magnetic coils 501, the plurality of shielding magnetic coils 502, the cryostat 503, the target 504, the axis 505, the gap 506, the opening 507, the recess 508, the MLC 510, and the primary collimator 512 may be similar to the plurality of main magnetic coils 401, the plurality of shielding magnetic coils 402, and the cryostat 403, the target 404, the axis 405, the gap 406, the opening 407, the recess 408, the MLC 410, and the primary collimator 412, and the descriptions thereof are not repeated herein.

Unlike the accelerator 409, the axis of the accelerating waveguide (tube) of the accelerator 509 may be parallel to the axis 505. Therefore, the accelerating waveguide (tube) may provide a linear path for accelerating the electrons along a beam path that is parallel to the axis 505 (also referred to as "parallel beam pass"). The plurality of main magnetic coils 501 and the plurality of shielding magnetic coils 502 may generate a magnetic field that is parallel or substantially parallel to the axis 505 (also referred to as "parallel magnetic field"). It shall be appreciated that the parallel magnetic field may pose least influence to the parallel beam pass. Therefore, the accelerator 509 may help reduce the influence of the magnetic field generated by the MRI device on the electrons. Similarly, the accelerating waveguide (tube) of the accelerator 509 may be at least partially surrounded by the magnetic shielding structure 511. The magnetic shielding structure 511 may be continuously distributed along the direction of the axis 505. In some embodiments, the magnetic shielding structure 511 may stretch to cover two ends of the accelerator along the direction of the axis, meaning that the magnetic shielding structure 511 may have a larger size than the accelerator 509 along the direction of the axis. The magnetic shielding structure 511 may be configured to further reduce the interference from the magnetic field generated by the MRI device. More descriptions regarding the embodiments with respect to the magnetic shielding structure may be found in, e.g., International Application No. PCT/CN2018/115394.

The deflection unit 513 may be configured to deflect the accelerated electrons from the parallel beam path onto the target 504. In some embodiments, the deflected electrons may perpendicularly impinge on the target 504, and therefore the deflection angle of the electrons may be 90 or 270 degrees. In some embodiments, the deflection unit 513 may include one or more magnets configured to provide a deflection magnetic field to deflect the accelerated electrons.

As shown in FIG. 5A, both of the accelerator 509 and the deflection unit 513 are disposed within the recess 508. In some embodiments, no shielding magnetic coil is arranged to "cover" the accelerator 509 and/or the deflection unit 513 along the radial direction of the cryostat 503. That is, there is no overlap between the axial positions of the plurality of shielding magnetic coils 502 and that of the accelerator 509 and/or the deflection unit 513. Further, the cryostat 503 may have a continuous body (i.e., a body which provides continuous fluid communication) along the radial direction of the cryostat 503, which accommodates both of the plurality of main magnetic coils 501 and the plurality of shielding magnetic coils 502.

The structure of the annular structure arrangement of the cryostat 503 may be the same as or similar to the cryostat 403 shown in FIG. 4A, FIG. 4B or FIG. 4C. As shown in FIG. 5A, the annular structure layer 521, the second annular structure 522 and the annular structure 523 may be arranged along a radial direction of the cryostat 503 (e.g., referring to the descriptions illustrated in FIG. 7). In some embodiments, the first annular structure 521 may refer to a vacuum vessel, the second annular structure 522 may refer to a thermal shield, and the third annular structure 523 may refer to a cryogen vessel. The multiple annular structures may enclose two chambers for containing a cooling medium. More descriptions regarding the multiple annular structures of the annular structure arrangement may be found in elsewhere in the present disclosure (e.g., FIGS. 4A-4C, and the descriptions thereof).

Figure 5B:
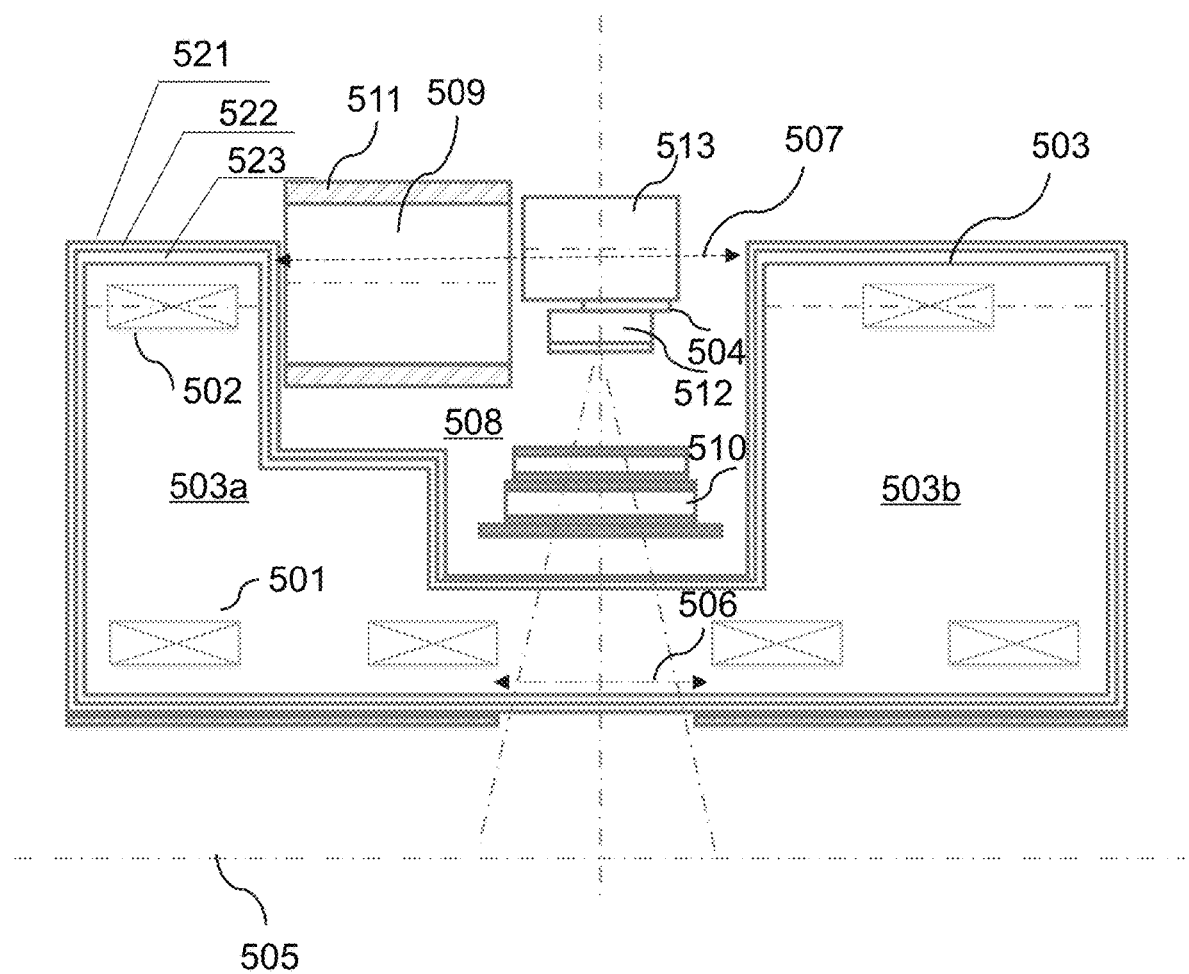
FIG. 5B shows a cross-sectional view of an upper portion of another exemplary therapeutic apparatus viewed along the X direction according to some embodiments of the present disclosure.

FIG. 5B shows a cross-sectional view of an upper portion of an exemplary therapeutic apparatus viewed along the X direction according to some embodiments of the present disclosure. Compared with the therapeutic apparatus 500 described in FIG. 5A, at least part of the accelerator 509 of the therapeutic apparatus 500' may be located at the outside of the recess 508 along the radial direction of the cryostat 503. As shown in FIG. 5B, the accelerator 509, the magnetic shielding structure 511 and the deflection unit 513 may at least partially stretch out of the opening 507 formed by the outer walls of the cryostat 503. In some embodiments, the accelerator 509 and the shielding structure 511 may be supported by or mounted to a gantry or a drum (e.g., the gantry 306 or the drum 312) that is capable of rotating around the axis 505.

Figure 5C:
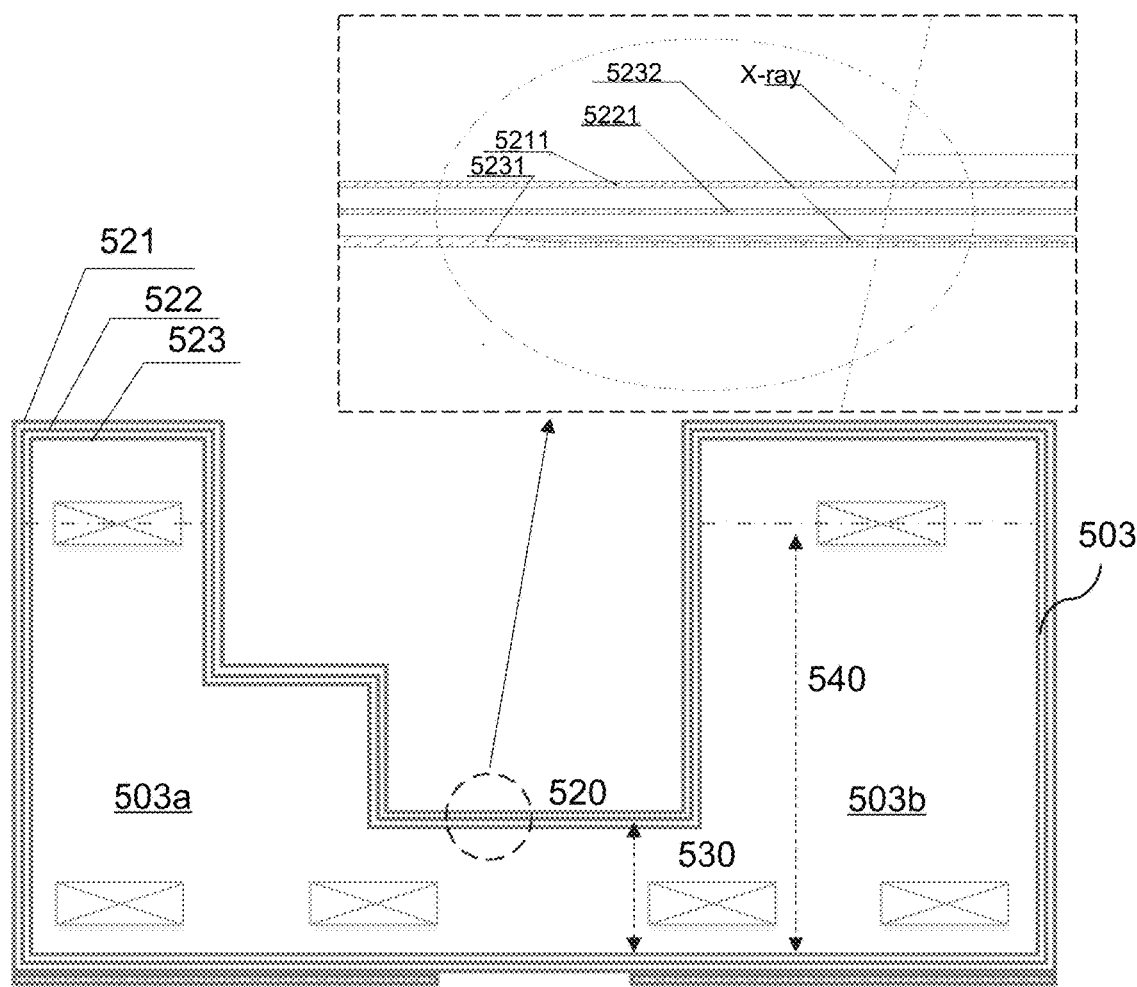
FIG. 5C shows a cross-sectional view of an upper portion of another exemplary cryostat viewed along the X direction according to some embodiments of the present disclosure.

FIG. 5C shows a cross-sectional view of an upper portion of an exemplary cryostat viewed along the X direction according to some embodiments of the present disclosure. As described in connection with FIG. 4C, the cryostat 503 may be similar to the cryostat 403. The first annular structure 521 may be made of stainless steel 5211, the second annular structure 522 may be made of aluminum 5221, and the third annular structure 523 may be made of stainless steel 5231 and a reinforcing material 5232 (e.g., carbon fiber). Compared with a conventional third annular structure made of only stainless steel, the effective thickness of the third annular structure 523 may be reduced due to a low density of the reinforcing material (compared to stainless steel). The effective thickness of the cryostat 503 may be reduced by reducing the effective thickness of the third annular structure 523. In this case, the degree of scattering of a radiation beam by passing through the cryostat 503 may be reduced. In addition, the cryostat 503 may include the first chamber 503a and the second chamber 503b in accordance with the theory of communicating vessel. The liquid levels of the first chamber 503a and the second chamber 503b may be at the same level. When the height 540 of the cooling medium (e.g., liquid helium) is higher than the height 530 of the neck portion of the cryostat 503, there does not exist a non cooling medium section in the neck portion. The degree of scattering of the radiation beam may be reduced during the radiation beam pass through the cooling medium section of the neck portion. Thus the radiation beam passed through the cryostat 503 may be relatively uniform. The radiotherapy quality may be improved accordingly. In some cases, when the neck portion is filled with the cooling medium, the dose of the radiation beam as it passes through the cryostat may be guaranteed, which won't be affected by a rotation angle of the radiation source. More descriptions of the structure of the cryostat 503 may be described in connection with FIG. 4C, and are not repeated herein.

In some embodiments, one or more level sensors may be mounted on the cryostat 503. The one or more level sensors may be configured to detect the liquid level of the cooling medium of each chamber of the cryostat 503. For example, when the liquid level of the cooling medium is lower than a level limit, the processing device 120 may generate an alert for notifying a user (e.g., an operator) to inject the cooling medium to the cryostat 503 through a cold head (not shown in FIG. 4C). In some embodiments, the level limit may be a value greater than the height 530. In some embodiments, the one or more level sensors may include a sight glass liquid level sensor, an ultrasonic sensor, a laser sensor, an infrared sensor, or the like, or any combination thereof.

It should be noted that the above description of the therapeutic apparatuses 500, and 500' is merely provided for the purposes of illustration, and not intended to limit the scope of the present disclosure. For persons having ordinary skills in the art, multiple variations and modifications may be made under the teachings of the present disclosure. For example, the primary collimator 512 and the MLC 510 may be integrated to form a single collimator. For another example, the neck portion illustrated in the cryostat 503 may not form an entire annulus. Specifically, the neck portion may be discrete arcs that connect the left chamber and the right chamber of the cryostat 503. Therefore, the neck portion may intermittently appear in the path of the radiation beam when the accelerator 509 rotates around the axis 505 to generate the radiation beam.

FIG. 6A shows a cross-sectional view of an upper portion of an exemplary therapeutic apparatus viewed along the X direction according to some embodiments of the present disclosure. As shown in FIG. 6A, the therapeutic apparatus 600 may include a plurality of main magnetic coils 601, a plurality of shielding magnetic coils 602, a cryostat 603 with an axis 605, a target 604, a first opening 607, a second opening 615, a recess 608, a accelerator 609, an MLC 610, a magnetic shielding structure 611, a primary collimator 612, and a deflection unit 613. The plurality of main magnetic coils 601, the plurality of shielding magnetic coils 602, the target 604, the axis 605, the first opening 607, the recess 608, the accelerator 609, the primary collimator 612, and the deflection unit 613 may be similar to the plurality of main magnetic coils 501, the plurality of shielding magnetic coils 502, the target 504, the axis 505, the opening 507, the recess 508, the accelerator 509, the primary collimator 512, and the deflection unit 513 and the descriptions are not repeated herein.

Compared with the MLC 510 shown in FIG. 5A, the MLC 610 may be located apart from the accelerator 609 along the radial direction such that the MLC 610 may be closer to, for example, the treatment region to be radiated. It shall be noted that the closer the distance between the MLC and the treatment region, the more accurate the shape of the radiation beam that irradiates on the treatment region may be controlled by the MLC.

The cryostat 603 may have a concave structure at the inner walls of the cryostat 603 to accommodate the MLC 610. Similar to the recess 608 that has the first opening 607 formed between the outer walls of the two chambers of the cryostat 603, the concave structure may have a second opening 615 formed between the inner walls of the two chambers of the cryostat 603. The concave structure may have the shape of an annulus and may be coaxial with the recess 608. The concave structure and the recess 608 may be separated by the neck portion of the cryostat 603. That is, the outermost surface of the neck portion forms the innermost boundary of the recess 608, and the innermost surface of the neck portion forms the outermost boundary of the concave structure. The concave structure may have a depth along the radial direction of the cryostat 603 that is larger than the height of the MLC 610 along the axis of the radiation beam. In some embodiment, one or more of the plurality of main magnetic coils 601 (e.g., 601a) may be arranged to surround the concave structure along the axis 605. The main magnetic coils 601a and the rest main magnetic coils in the left/right chamber of the cryostat 603 may form a step structure. The main magnetic coils 601a may have a larger radius from the axis 605 than that of the rest main magnetic coils. Further, a gap 606 may be formed between the main magnetic coils 601a, allowing the radiation beam to pass through. In some embodiments, no main magnetic coil is arranged to surround the concave along the axis 605, and thus all the plurality of main magnetic coils 601 may be arranged to surround the inner walls of the cryostat 603 and have the same radius from the axis 605.

Figure 6B:
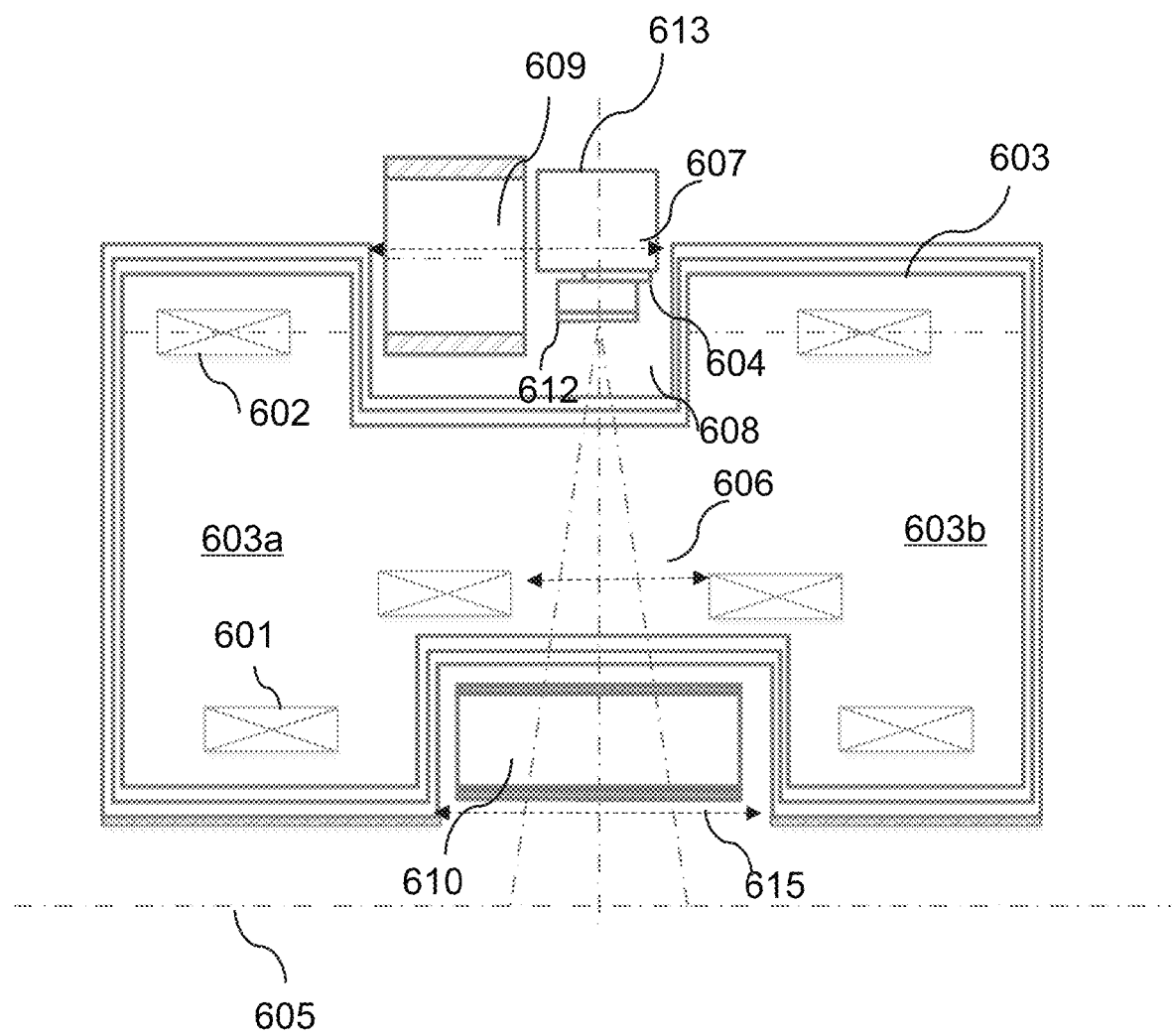
FIG. 6B shows a cross-sectional view of an upper portion of another exemplary therapeutic apparatus viewed along the X direction according to some embodiments of the present disclosure.

FIG. 6B shows a cross-sectional view of an upper portion of an exemplary therapeutic apparatus viewed along the X direction according to some embodiments of the present disclosure. Compared with the therapeutic apparatus 600 described in FIG. 6A, at least part of the accelerator 609 of the therapeutic apparatus 600' may be located at the outside of the recess 608 along the radial direction of the cryostat 603. As shown in FIG. 6B, the accelerator 609, the shielding structure 611 and the deflection unit 613 may at least partially stretch out of the opening 607 formed by the outer walls of the cryostat 603. In some embodiments, the accelerator 609, the shielding structure 611, and the deflection unit 613 may be supported by or mounted to a gantry or a drum (e.g., the gantry 306 or the drum 312) that is configured to rotate around the axis 605.

Figure 6C:
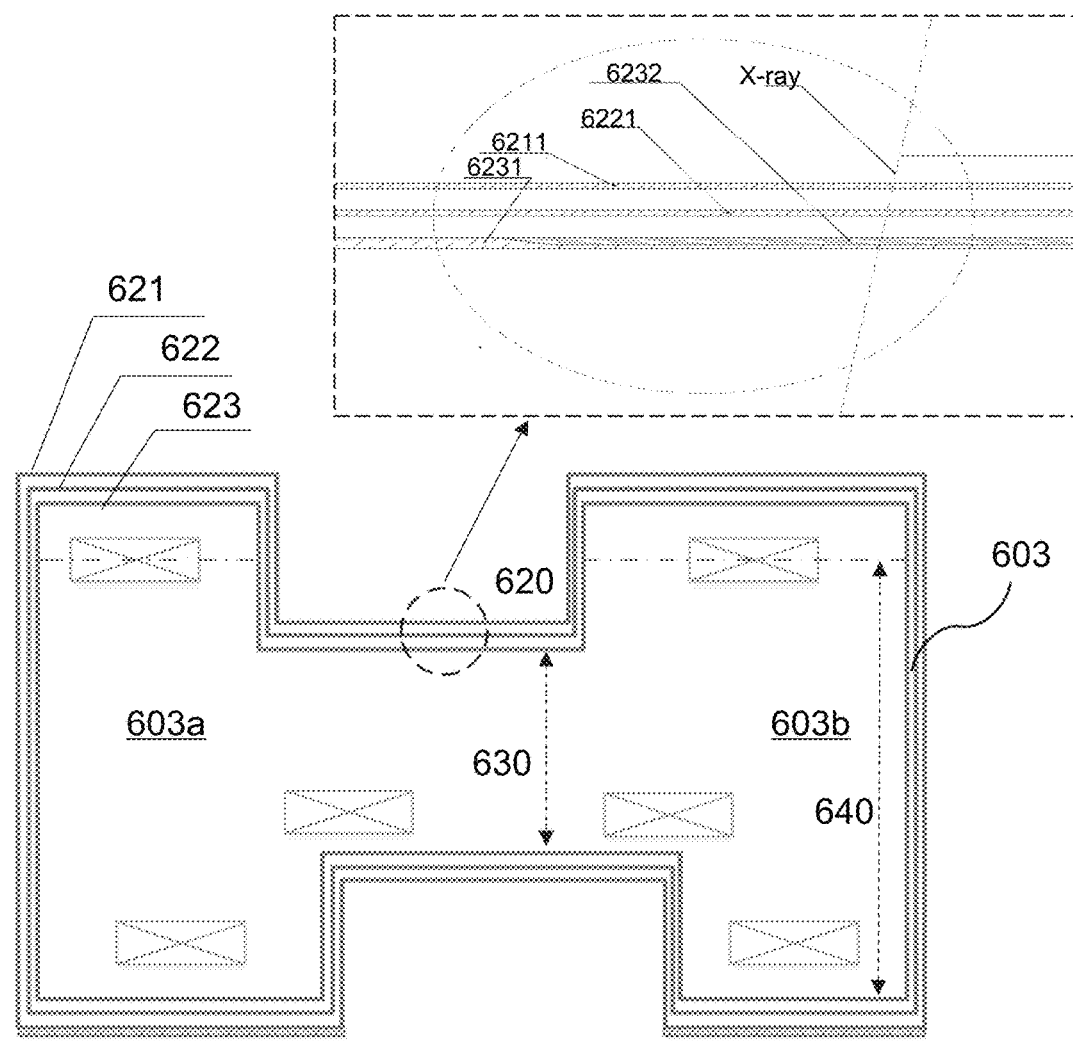
FIG. 6C shows a cross-sectional view of an upper portion of another exemplary cryostat viewed along the X direction according to some embodiments of the present disclosure.

FIG. 6C shows a cross-sectional view of an upper portion of an exemplary cryostat viewed along the X direction according to some embodiments of the present disclosure. As described in connection with FIG. 4C or FIG. 5C, in the cryostat 603, the first annular structure 621 may be made of stainless steel 6211, the second annular structure 622 may be made of aluminum 6221, and the third annular structure 623 may be made of stainless steel 6231 and a reinforcing material 6232 (e.g., carbon fiber). Compared with a conventional third annular structure made of only stainless steel, the effective thickness of the third annular structure 623 may be reduced due to a low density of the reinforcing material (compared with stainless steel). The effective thickness of the cryostat 603 may be small by reducing the effective thickness of the third annular structure 623. In this case, the degree of scattering may be reduced during the radiation beam passing through the cryostat 603. In addition, the cryostat 603 may include a first chamber 603a and a second chamber 603b in accordance with the theory of communicating vessel. The liquid levels of the first chamber 603a and the second chamber 603b may be at the same level. When the height 640 of the cooling medium (e.g., liquid helium) is higher than the height 630 of the neck portion of the cryostat, there does not exist a non cooling medium section in the neck portion. The degree of scattering of the radiation beam may be reduced during the radiation beam passing through the uniform cooling medium of the neck portion. Thus the radiation beam passed through the cryostat 603 may be relatively uniform. The radiotherapy effect may be improved accordingly. In some cases, when the neck portion is filled with the cooling medium, the dose of the radiation beam as it passes through the cryostat may be guaranteed, which won't be affected by a rotation angle of the radiation source. More descriptions of the structure of the cryostat 603 may be described in connection with FIG. 4C or FIG. 5C, and are not repeated herein.

In some embodiments, one or more level sensors may be mounted on the cryostat 603. The one or more level sensors may be configured to detect the liquid level of the cooling medium of each chamber of the cryostat 503. For example, when the liquid level of the cooling medium is lower than a level limit, the processing device 120 may generate an alert for notifying a user (e.g., an operator) to inject the cooling medium to the cryostat 603 through a cold head (not shown in FIG. 4C). In some embodiments, the level limit may be a value greater than the height 630. In some embodiments, the one or more level sensors may include a sight glass liquid level sensor, an ultrasonic sensor, a laser sensor, an infrared sensor, or the like, or any combination thereof.

It should be noted that the above description of the therapeutic apparatus 600 or 600' is merely provided for the purposes of illustration, and not intended to limit the scope of the present disclosure. For persons having ordinary skills in the art, multiple variations and modifications may be made under the teachings of the present disclosure. For example, the neck portion illustrated in the cryostat 603 may not form an entire annulus. Specifically, the neck portion may be discrete arcs that connect the left chamber and the right chamber of the cryostat 603. Therefore, the neck portion may intermittently appear in the path of the radiation beam when the accelerator 609 rotates around the axis 605 to generate the radiation beam.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein.

These alterations, improvements, and modifications are intended to be suggested by the present disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A therapeutic apparatus comprising:
a magnetic resonance imaging (MRI) device configured to acquire MRI data with respect to a region of interest (ROI), wherein the MRI device includes an annular cryostat, the annular cryostat including:
one or more chambers arranged along an axis of the annular cryostat;
an annular structure arrangement enclosing the one or more chambers, wherein the annular structure arrangement includes multiple annular structures, and a portion of at least one of the multiple annular structures is made of a metallic material and a reinforcing material; and
at least a recess disposed on the annular cryostat, the recess having an opening formed on an outer surface of the annular structure arrangement; and
a radiation therapy device configured to apply therapeutic radiation to at least one portion of the ROI, the radiation therapy device including:
an accelerator configured to accelerate electrons in an electron beam to produce a radiation beam of the therapeutic radiation, the accelerator at least partially located within the recess of the annular cryostat; and
one or more collimation components configured to shape the radiation beam;
wherein:
the one or more chambers include two chambers being in communication through a neck portion of the annular cryostat,
the recess is at least defined by the two chambers and the neck portion of the annular cryostat, the two chambers and the neck portion of the annular cryostat enclosing a cooling medium, and
the recess accommodates a target configured to produce the radiation beam, such that a radial position of the target that in the opening is closer to the axis of the annular cryostat than an outermost radial position of the multiple annular structures.

2. The therapeutic apparatus of claim 1, wherein the annular structure arrangement includes:
a first annular structure configured to provide a vacuum space enclosing the one or more chambers;

a second annular structure configured to reduce heat transfer from the first annular structure to a third annular structure; and a third annular structure configured to contain a cooling medium, at least one of the first annular structure, the second annular structure, or the third annular structure being made of the metallic material and the reinforcing material.

3. The therapeutic apparatus of claim 1, wherein the reinforcing material has one or more characteristics of a low density, a high mechanical strength, a radiation-resistance, or a heat-resistance.

4. The therapeutic apparatus of claim 1, wherein the annular cryostat further includes one or more sensors configured to detect a liquid level of a cooling medium of each of the one or more chambers of the annular cryostat.

5. The therapeutic apparatus of claim 1, wherein the accelerator is surrounded by at least one shielding structure, wherein the magnetic structure includes a plurality of magnetic shielding layers, and at least one of the plurality of magnetic shielding layers is used to reduce magnetic interference between one or more components of the MRI device and the radiation therapy device.

6. The therapeutic apparatus of claim 1, wherein the electron beam moves along an electron beam path that is parallel to the axis of the annular cryostat, and the radiation therapy device further includes:
a target; and
a beam deflection unit configured to deflect the electrons in the electron beam onto the target to produce the radiation beam of the therapeutic radiation.

7. The therapeutic apparatus of claim 1, wherein the multiple annular structures include a first annular structure, a second annular structure, and a third annular structure, wherein
the first annular structure encloses the second annular structure, and the second annular structure encloses the third annular structure,
outer and inner surfaces of the first annular structure, the second annular structure, and the third annular structure are arranged along a radial direction of the cryostat, and
at least one of the first annular structure, the second annular structure, or the third annular structure is made of the metallic material and the reinforcing material.

8. The therapeutic apparatus of claim 1, wherein at least part of the portion of the at least one of the multiple annular structures traversed by the radiation beam includes a metallic material layer and a reinforcing material layer stacked along a radiation direction of the radiation beam.

9. The therapeutic apparatus of claim 8, wherein an effective thickness of any of the multiple annular structures made of the metallic material and the reinforcing material is smaller than an effective thickness of any of the multiple annular structures made of the metallic material.

10. The therapeutic apparatus of claim 1, wherein the reinforcing material includes at least one of a carbon fiber, an aramid fiber, a silicon carbide (SiC) fiber, an asbestos fiber, a crystal whisker, a graphene fiber, or an alloy material.

11. The therapeutic apparatus of claim 1, wherein the recess has a depth defined by a distance from the opening of the recess to an outermost surface of the neck portion of the annular cryostat in a radial direction.

12. The therapeutic apparatus of claim 11, wherein
the annular cryostat has a concave structure at the inner walls of the annular cryostat to accommodate a multi-leaf collimator (MLC),
the concave structure has a second opening formed between inner walls of two of the one or more chambers of the annular cryostat,
the concave structure and the recess are separated by the neck portion of the annular cryostat, an outermost surface of the neck portion forming an innermost boundary of the recess, the innermost surface of the neck portion forming the outermost boundary of the concave structure, and
the concave structure has a depth along the radial direction of the annular cryostat that is larger than a height of the MLC along an axis of the radiation beam.

13. The therapeutic apparatus of claim 1, wherein the therapeutic apparatus further includes one or more processing devices, the one or more processing devices are configured to:
acquire the MRI data with respect to the ROI using the MRI device;
reconstruct an MRI image related to at least one portion of the ROI based on the MRI data;
determine a parameter associated with a size of the at least one portion of the ROI based on the MRI image, wherein the parameter associated with the size of the at least one portion of the ROI indicates the shape of a characteristic cross section of a tumor;
generate a control signal according to the parameter associated with the size of at least one portion of the ROI;
send the control signal to the radiation therapy device to cause the radiation therapy device to apply the therapeutic radiation.

14. The therapeutic apparatus of claim 1, wherein all parts of the neck portion through which the radiation beam passes is filled with the cooling medium when a radiation source of the therapeutic apparatus rotates at various angles.

15. The therapeutic apparatus of claim 14, wherein
the neck portion are discrete arcs that connect a left chamber and a right chamber of the annular cryostat, and
the neck portion intermittently appears in a path of the radiation beam when the accelerator rotates around the axis to generate the radiation beam.

16. The therapeutic apparatus of claim 14, wherein the radiation source is rotatably arranged in the recess, and the radiation source is configured to:
emit the radiation beam when the radiation source rotates to certain angles; or
pause at a desired position and emit the radiation beam for a specific duration when the radiation source rotates to the desired position, then resume to rotate; or
continuously rotate and emit the radiation beam continuously or intermittently; or
continuously emit the radiation beam while rotating.

17. A magnetic resonance imaging (MRI) device comprising an annular cryostat, the annular cryostat including:
one or more chambers arranged along an axis of the annular cryostat; and
an annular structure arrangement enclosing the one or more chambers, wherein the annular structure arrangement includes multiple annular structures, and a portion of at least one of the multiple annular structures is made of a metallic material and a reinforcing material; and
at least a recess disposed on the annular cryostat, the recess having an opening formed on an outer surface of the annular structure arrangement, and an accelerator at least partially located within the recess of the annular cryostat;

wherein:
the one or more chambers include two chambers being in communication through a neck portion of the annular cryostat,
the recess is at least defined by the two chambers and the neck portion of the annular cryostat, the two chambers and the neck portion of the annular cryostat enclosing a cooling medium, and
the recess accommodates a target configured to produce the radiation beam, such that a radial position of the target that in the opening is closer to the axis of the annular cryostat than an outermost radial position of the multiple annular structures.

18. The MRI device of claim 17, wherein all parts of the neck portion through which the radiation beam passes is filled with the cooling medium when a radiation source of the therapeutic apparatus rotates at various angles.

19. A therapeutic apparatus comprising:
a magnetic resonance imaging (MRI) device configured to acquire MRI data with respect to a region of interest (ROI), wherein the MRI device includes an annular cryostat, the annular cryostat including:
one or more chambers arranged along an axis of the annular cryostat; an annular structure assembly enclosing the one or more chambers, wherein
the annular structure arrangement includes multiple annular structures, and a portion of at least one of the multiple annular structures is made of a metallic material and a reinforcing material; and
at least a recess disposed on the annular cryostat, the recess having an opening formed on an outer surface of the annular structure arrangement; and a radiation therapy device configured to apply therapeutic radiation to at least one portion of the ROI, the radiation therapy device including:
an accelerator configured to accelerate electrons in an electron beam along an electron beam path that is parallel to the axis, the accelerator at least partially located within the recess of the annular cryostat;
a target; and
a beam deflection unit configured to deflect the electrons from the electron beam onto the target to produce a radiation beam of the therapeutic radiation;
wherein:
the one or more chambers include two chambers being in communication through a neck portion of the annular cryostat,
the recess is at least defined by the two chambers and the neck portion of the annular cryostat, the two chambers and the neck portion of the annular cryostat enclosing a cooling medium, and
the recess accommodates a target configured to produce the radiation beam, such that a radial position of the target that in the opening is closer to the axis of the annular cryostat than an outermost radial position of the multiple annular structures.

20. The therapeutic apparatus of claim 19, wherein the accelerator is surrounded by at least one shielding structure, the magnetic shielding structure includes a plurality of magnetic shielding layers, and at least one of the plurality of magnetic shielding layers is used to reduce magnetic interference between one or more components of the MRI device and the radiation therapy device.

* * * * *